United States Patent
Shastri et al.

(10) Patent No.: US 11,202,852 B2
(45) Date of Patent: Dec. 21, 2021

(54) BIOMATERIALS FOR NEURONAL IMPLANTS AND USE OF SAID BIOMATERIALS IN THE DIAGNOSIS AND THERAPY OF NEURONAL DISEASES

(71) Applicant: Albert-Ludwigs-Universitat Freiburg, Freiburg (DE)

(72) Inventors: Prasad Shastri, Breisach (DE); Nils Blumenthal, Freiburg (DE)

(73) Assignee: ALBERT-LUDWIGS-UNIVERSITAT FREIBURG, Freiburg (DE)

(*) Notice: Subject to any disclaimer, the term of this patent is extended or adjusted under 35 U.S.C. 154(b) by 935 days.

(21) Appl. No.: 15/518,244

(22) PCT Filed: Oct. 9, 2015

(86) PCT No.: PCT/EP2015/073426
§ 371 (c)(1),
(2) Date: Apr. 17, 2017

(87) PCT Pub. No.: WO2016/055622
PCT Pub. Date: Apr. 14, 2016

(65) Prior Publication Data
US 2017/0252486 A1    Sep. 7, 2017

(30) Foreign Application Priority Data

Oct. 10, 2014   (EP) .................................... 14188556

(51) Int. Cl.
*A61L 27/50*       (2006.01)
*A61L 27/36*       (2006.01)
(Continued)

(52) U.S. Cl.
CPC ................ *A61L 27/50* (2013.01); *A61B 5/24* (2021.01); *A61L 27/3675* (2013.01); *A61N 1/04* (2013.01);
(Continued)

(58) Field of Classification Search
CPC .. A61L 27/50; A61L 27/3675; A61L 2400/12; A61B 5/04; A61B 5/04001;
(Continued)

(56) References Cited

U.S. PATENT DOCUMENTS

2007/0038307 A1    2/2007  Webster
2007/0060815 A1*   3/2007  Martin ...................... A61B 5/25
                                                    600/372
(Continued)

FOREIGN PATENT DOCUMENTS

WO    2006014493 A2    2/2006
WO    2014116132 A1    7/2014
(Continued)

OTHER PUBLICATIONS

Surface Roughness Conversion Chart Tables. Datasheet [online]. Engineer's Edge, Jul. 2, 2014 [Retrieved on Sep. 3, 2020], Retrieved from the Internet: <URL: https://web.archive.org/web/20140702060217/ https://www.engineersedge.com/manufacturing/surface-roughness-conversion.htm>. (Year: 2014).*
(Continued)

*Primary Examiner* — Eun Hwa Kim
*Assistant Examiner* — Adam Z Minchella
(74) *Attorney, Agent, or Firm* — Gary M. Myles; Myles Intellectual Property Law

(57) ABSTRACT

The present invention relates to a neural implant comprising a biomaterial having an outer surface with a stochastic nanoroughness (Rq), and the application of said stochastic nanoroughness in the diagnosis and/or treatment of a neurological disorder, such as, for example, Parkinson's disease, Alzheimer's disease, glioblastoma and/or for disrupting and/or preventing glial scars in the context of
(Continued)

mammalian mechanosensing ion channels selected from the family of PIEZO-1 and PIEZO-2 ion channels.

14 Claims, 14 Drawing Sheets

Specification includes a Sequence Listing.

(51) Int. Cl.
| | | |
|---|---|---|
| *A61N 1/04* | (2006.01) | |
| *G01N 33/50* | (2006.01) | |
| *A61N 1/05* | (2006.01) | |
| *A61B 5/24* | (2021.01) | |
| *G01N 33/68* | (2006.01) | |
| *A61B 5/00* | (2006.01) | |

(52) U.S. Cl.
CPC ......... *A61N 1/0531* (2013.01); *A61N 1/0536* (2013.01); *A61N 1/0551* (2013.01); *G01N 33/502* (2013.01); *G01N 33/5023* (2013.01); *G01N 33/5058* (2013.01); *G01N 33/68* (2013.01); *A61B 5/4082* (2013.01); *A61B 5/4088* (2013.01); *A61L 2400/12* (2013.01)

(58) Field of Classification Search
CPC ...... A61B 5/4082; A61B 5/4088; A61N 1/04; A61N 1/0531; A61N 1/0536; A61N 1/0551; G01N 33/5058; G01N 33/68; G01N 33/502; G01N 33/5023
See application file for complete search history.

(56) References Cited

U.S. PATENT DOCUMENTS

| | | | | |
|---|---|---|---|---|
| 2011/0268776 | A1* | 11/2011 | Schapira | A61L 27/50 |
| | | | | 424/400 |
| 2015/0014891 | A1* | 1/2015 | Amatucci | C23F 4/02 |
| | | | | 264/447 |
| 2016/0073887 | A1* | 3/2016 | Lee | A61N 5/0622 |
| | | | | 600/377 |

FOREIGN PATENT DOCUMENTS

| | | | | |
|---|---|---|---|---|
| WO | WO 2014/116132 | * | 7/2014 | ........... A61K 31/765 |
| WO | WO-2014/116132 | * | 7/2014 | ........... A61K 31/765 |
| WO | WO-2014116132 A1 | * | 7/2014 | ............. A61L 31/10 |
| WO | 2016055622 A1 | | 4/2016 | |

OTHER PUBLICATIONS

Suchyna, Bilayer-dependent inhibition of mechanosensitive channels by neuroactive peptide enantiomers, Nature, 2004, pp. 235-240, vol. 430.

Satoh, A novel membrane protein, encoded by the gene covering KIAA0233, is transcriptionally induced in senile plaque-associated astrocytes, Brain Research, 2006, pp. 19-27, vol. 108.

Pennisi, Nanoscale topography reduces fibroblast growth, focal adhesion size and migration-related gene expression on platinum surfaces, Colloids and Surfaces B: Biointerfaces, 2011, pp. 189-197, vol. 85.

Blumenthal, Stochastic nanoroughness modulates neuron-astrocyte interactions and function via mechanosensing cation channels, Proceedings of the National Acadamy of Science USA, 2014, pp. 16124-16129, vol. 111(45).

Theodosis, Activity-dependent structural and functional plasticity of astrocyte-neuron interactions, Physiology Review, 2008, pp. 983-1008, vol. 88.

International Search Report and Written Opinion of the International Searching Authority dated Dec. 4, 2015 in PCT Patent Application No. PCT/EP2015/073426.

International Search Report and Written Opinion of the International Searching Authority dated Feb. 18, 2016 in PCT Patent Application No. PCT/EP2015/073426.

International Search Report and Written Opinion of the International Searching Authority dated May 9, 2016 in PCT Patent Application No. PCT/EP2015/073426.

* cited by examiner

A)

SEQUENCE LISTING

```
<160> NUMBER OF SEQ ID NOS: 4

<210> SEQ ID NO 1
<211> LENGTH: 19
<212> TYPE: RNA
<213> ORGANISM: Homo sapiens

<400> SEQUENCE: 1
gcacaaaggc cuccgacuu                                                        19

<210> SEQ ID NO 2
<211> LENGTH: 19
<212> TYPE: RNA
<213> ORGANISM: Homo sapiens

<400> SEQUENCE: 2
ggguugaaga uucgggaga                                                        19

<210> SEQ ID NO 3
<211> LENGTH: 19
<212> TYPE: RNA
<213> ORGANISM: Homo sapiens

<400> SEQUENCE: 3
cggaagaaug gcagcgcau                                                        19

<210> SEQ ID NO 4
<211> LENGTH: 19
<212> TYPE: RNA
<213> ORGANISM: Homo sapiens

<400> SEQUENCE: 4
cagaugaaca guugggcga                                                        19
```

BIOMATERIALS FOR NEURONAL IMPLANTS AND USE OF SAID BIOMATERIALS IN THE DIAGNOSIS AND THERAPY OF NEURONAL DISEASES

CROSS-REFERENCE TO RELATED APPLICATIONS

This U.S. non-provisional patent application is a U.S. national stage application, which was filed on Apr. 10, 2017 under 35 U.S.C. § 371 and claims priority to PCT Patent Application No. PCT/EP2015/073426, which was filed on Oct. 9, 2015, and to European Patent Application No. EP14188556.6, which was filed on Oct. 10, 2014. The contents of PCT Patent Application No. PCT/EP2015/073426 and European Patent Application No. EP14188556.6 are incorporated herein by reference in their entirety.

SEQUENCE LISTING

The present application includes a Sequence Listing in electronic format as a txt file entitled "ALUF-01-0103USWO_2017-07-07_U30584WOUS_U.S. Ser. No. 15/518,244_SEQLIST_ST25," which was created on Jul. 7, 2017 and which has a size of 1,033 bytes. The contents of txt file "ALUF-01-0103USWO_2017-07-07_U30584-WOUS_U.S. Ser. No. 15/518,244_SEQLIST_ST25" are incorporated by reference herein."

The present invention relates to a neural implant comprising a biomaterial having an outer surface with a stochastic nanoroughness (Rq), and the application of said stochastic nanoroughness in the diagnosis and/or treatment of a neurological disorder, such as, for example, Parkinson's disease, Alzheimer's disease, glioblastoma and/or for disrupting and/or preventing glial scars. For the purposes of the present invention, all the references as cited herein are incorporated by reference in their entireties.

Controlling cellular responses on biomaterial surfaces is crucial in biomedical applications such as tissue engineering and implantable prosthetics. Since cells encounter various nanoscale topographic features in their natural environment, it has been postulated that surface nanotopography may be an alternative route to fabricate biomaterials with a desirable cellular response.

Engineered surfaces are created in various ways, typically by machining, surface treatment and coating. Most often a combination of various machining, treatment and coating operation are used to produce surfaces with characteristics that are desirable for particular application. Each surface generation process produces surface topography characteristic of the process and process variables used. Surface topography, therefore, contains signature of the surface generation process and as such can be used to diagnose, monitor and control the manufacturing process. Surface topography establishes a correspondence between an engineering surface phenomenon (e.g. wear, chatter, etc.) and its topographical characteristics (e.g. bearing area, oil retention volume etc.). A surface profile may be composed of a range of frequency components. The high frequency (or short wave) components correspond to those that are perceived to be rough and hence called "roughness". The low frequency (or long wave) components correspond to more gradual changes in the profile and are often associated with the terms "waviness" or even "form". The waviness or the low frequency component is periodic in nature, while the high frequency component or the roughness is random. Different frequency components in a surface profile can be separated out by a procedure called as filtering. The random surface roughness is the characteristic of any machining process and is characterized by many amplitude and statistical parameters.

Lipski et al. (in: A M Lipski, C Pino, F R Haselton, I-W. Chen and V P Shastri "The effect of silica nanoparticle-modified surfaces on cell morphology, cytoskeletal organization and function", Biomaterials, (28), 3836 (2008)) investigate the effect of nanoparticle (NP) assemblies arranged on a flat substrate on cytoskeletal organization, proliferation and metabolic activity on two cell types. To vary roughness without altering chemistry, glass substrates were coated with monodispersed silica nanoparticles of 50, 100 and 300 nm in diameter. The impact of surface roughness at the nanoscale on cell morphology was studied by quantifying cell spreading, shape, cytoskeletal F-actin alignment, and recruitment of focal adhesion complexes (FAC) using image analysis. In the two cell types tested, surface roughness introduced by nanoparticles had cell type specific effects on cell morphology and metabolism. Interestingly, for both cell types surface roughness promoted the formation of long, thick F-actin fibers, which aligned with the long axis of each cell. Their finding that nanoroughness, as imparted by nanoparticle assemblies, effects cellular processes in a cell specific manner, can have far reaching consequences on the development of "smart" biomaterials especially for directing stem cell differentiation.

Pennisi et al. (in: Pennisi C P, Dolatshahi-Pirouz A, Foss M, Chevallier J, Fink T, Zachar V, Besenbacher F, Yoshida K. Nanoscale topography reduces fibroblast growth, focal adhesion size and migration-related gene expression on platinum surfaces. Colloids Surf B Biointerfaces. 2011 Jul. 1; 85 (2):189-97. Epub 2011 Feb. 26) describes an investigation of the responses of primary human fibroblasts to platinum substrates with different levels of surface roughness at the nanoscale. The nanorough surfaces were fabricated by using the glancing angle deposition technique (GLAD). The levels of cellular responses were found to depend on the surface roughness and the size of the nanoscale features. The authors showed that in response to nanotopography cells spread less and have an elongated morphology, displaying signs of actin cytoskeleton impairment and reduced formation of focal adhesion complexes. Although cell growth and adhesion were impaired on the nanorough substrates, cell viability was not affected by topography. To a minor extent the results also indicated that cell migration might be reduced on the nanorough surfaces, since a significantly lower gene expression of migration related genes were found on the roughest surfaces as compared to the flat reference. The authors conclude that that surface nanotopography influences fibroblasts responses on platinum, which may be used to reduce cellular adhesion on platinum implant surfaces such as implantable neural electrodes.

Seil and Webster (in: Decreased astroglial cell adhesion and proliferation on zinc oxide nanoparticle polyurethane composites. Int J Nanomedicine. December 2008; 3 (4): 523-531) describe a study on the activity of astroglial cells on ZnO nanoparticle polymer composites. ZnO nanoparticles embedded in polyurethane were analyzed via scanning electron microscopy to evaluate nanoscale surface features of the composites. The surface chemistry was characterized via X-ray photoelectron spectroscopy. Astroglial cell response was evaluated based on cell adhesion and proliferation. Astrocyte adhesion was significantly reduced on ZnO nanoparticle/polyurethane (PU) composites with a weight ratio of 50:50 (PU:ZnO) wt. %, 75:25 (PU:ZnO) wt. %, and 90:10 (PU:ZnO) wt. % in comparison to pure PU. The successful production of ZnO nanoparticle composite scaffolds suitable for decreasing astroglial cell density demonstrated their potential as a nerve guidance channel material.

WO 2006014493 A2 describes a peptide and its variants that blocks stretch-activated ion channels. The peptide, designated as D-GsMTx4, is an enantiomer of a peptide GsMTX-4 present in the venom of the spider *Grammostola spatulata*.

Glial scar formation around implanted electrodes soon after implantation into the brain leads to dysfunction of these electrodes. The formation of glial scars around implantable brain electrodes is the dominant contributor to electrode failure. Discovering strategies to inhibit glial scar formation around brain implants is critical for long term electrode function and would thus lead to improvement of treating patients with neurological disorders such as epilepsy or Parkinson's disease.

Amongst other components, the central nervous system (CNS) is also comprised of extracellular matrix macromolecules and glia support cells, and the contribution of the physical attributes of these components in the maintenance and regulation of neuronal function is not well understood. These components possess well-defined topography.

In the context of neuronal development and neurophysiology, astrocytes have an established role in maintaining neuronal function. They form a vast network that provides the physical and biochemical matrix over which neurons thrive and function (see, for example, Theodosis D, Poulain D, Oliet S (2008) Activity-dependent structural and functional plasticity of astrocyte-neuron interactions. Physiol Rev: 983-1008. Wade J J, McDaid L J, Harkin J, Crunelli V, Kelso J a S (2011) Bidirectional coupling between astrocytes and neurons mediates learning and dynamic coordination in the brain: a multiple modeling approach. PLoS One 6: e29445).

The plasticity found in the brain can be attributed in part to the morphological changes that occur in astrocyte processes that can alter not only the geometry of the neuronal environment but also induce dynamic changes in astrocyte-neuron interactions impacting neurotransmission, signal gradients and the relationship between synapses. Interestingly, the changes to the neuronal environment induced by astrocytes involve extracellular matrix (ECM) molecules such as proteoglycans (PGs), postulating a significant role for topography in neural development.

A glioma is a type of tumor that starts in the brain or spine. It is called a glioma because it arises from glial cells, such as astrocytes. Gliomas make up about 30% of all brain and central nervous system tumors and 80% of all malignant brain tumors. Glioblastoma multiforme is a malignant astrocytoma and the most common primary brain tumor among adults.

Alzheimer's disease is characterized by loss of neuronal function in the central nervous system (CNS). This loss of function occurs predominantly around senile plaques, which mainly consist of amyloid-beta deposits. The exact mechanism by which neuronal death and loss of function occur is currently not well understood.

Currently therapies are focused on dissolving the beta amyloid deposits and this approach has not been very successful. One approach is to use cholera toxin-B covalently linked to myelin basic protein. Therapies based on anti-amyloid beta plaque antibodies (e.g. Bapineuzumab) jointly developed by Johnson & Johnson and Pfizer have failed in Phase III clinicals. Recently in July of 2014, another beta amyloid plaque targeted antibody (Crenezumab) developed by Roche/Genentech failed to meet its phase II objectives. Thus, there is real need for developing new targets for preventing or reversing loss of neuronal function due to Alzheimer's.

Satoh et al. (in: Satoh K, Hata M, Takahara S, Tsuzaki H, Yokota H, Akatsu H, Yamamoto T, Kosaka K, Yamada T. A novel membrane protein, encoded by the gene covering KIAA0233, is transcriptionally induced in senile plaque-associated astrocytes. Brain Res. 2006 Sep. 7; 1108 (1):19-27. Epub 2006 Jul. 18) in an effort to identify astrocyte-derived molecules that may be intimately associated with progression of AD, identified a novel Abeta-induced rat gene, designated Mib, whose human counterpart covers KIAA0233. In AD brains, Mib is expressed in activated astrocytes associated with senile plaques, but not expressed in neurons around lesions. From these observations, Mib appears to be a novel Amyloid-beta-responsive gene that may play a role in astrocyte inflammatory activation around senile plaques in the AD brain.

In order to solve the above objects, the present inventors have developed biomaterial surfaces with properties that interfere with the organization of astroglia and fibroblasts, which is necessary for the formation of, for example, a glial scar.

Thus, in a first aspect of the present invention, the object of the present invention is solved by a neural implant comprising a biomaterial having an outer surface with a stochastic nanoroughness (Rq) of between 25 and 40 nm, preferably of between 32 nm+/−5 nm, and most preferred of about 32 nm.

The present invention comprises biomaterial surfaces, either as the surface as such and/or as coatings, with specific topographies found to alter astrocyte phenotype. The surface or coating generates a nanotopography with a specific roughness on the implant surface and is thereby able to prevent problems common with current implants, such as, for example, glial scar formation around the implant in vitro and/or vivo.

US 2007-0038307 describes nanomaterials for neural and orthopedic prostheses. Composite carbon nanofibers enhance neuronal growth and minimize glial scar tissue formation. Methods and compositions to promote neuronal growth and minimize scar tissue formation during prolonged monitoring and treatment of neural tissue are disclosed. Composite polyurethane carbon nanofiber is a suitable material for neural implant. Composite carbon nanomaterials decrease adhesion of astrocytes and fibroblasts.

The neural implant can be made out of any of a variety of materials known to be suitable for serving as (part of) a neural implant, preferably as described herein. Preferred is the neural implant according to the present invention, wherein said biomaterial is selected from platinum, synthetic polymers, for example poly(organo)siloxanes, antimicrobial polymers, materials impregnated/coated with carbon nanotubes (CNTs) and/or graphene, polypyrrole (PPy), poly (3,4-ethylene dioxythiophene) (PEDOT), polyterthiophene (PTTh), Cyclotene®, and parylene C.

Further preferred is a neural implant according to the present invention, wherein said implant comprises a component selected from a polymer wire, a nanotube, an array of micro-sized posts or pillars, carbon fibers, and composite carbon nanofibers.

A wide variety of biomaterials are used in neural implants for the central nervous system (CNS): drugs or gene carriers for treatment of neurological disorders and brain tumors, scaffolds for promoting tissue regeneration, neural electrodes for restoration of lost neurological functions or shunt systems for hydrocephalus. The biomaterials used in the CNS include silicone, lipids, natural polymers and synthetic polymers in various forms based on their applications. Some applications, such as neural electrodes or CNS shunts, require the biomaterials to remain functional indefinitely. Other applications, such as drug carriers or tissue scaffolds, require the biomaterials to degrade after their function is fulfilled. For a review regarding biomaterials that can be used in the context of the present invention, see, for example, Zhong Y and Bellamkonda R V (Biomaterials for the central nervous system. J R Soc Interface. 2008 Sep. 6; 5 (26):957-75).

Usually, neural implants, such as electrodes for brain implantation, are made out of polymers, metals or a combination of both. Material coatings for these electrodes are not widely used. The surprising advantage of the present invention is the creation of nanotopography on implant surfaces which allows for a control of the behavior of surrounding cells (especially astrocytes which are a main contributor in, for example, glial scar formation).

Tissue fibrosis, or scar formation, is a common response to damage in most organs of the body. The central nervous system (CNS) is special in that fibrogenic cells are restricted to vascular and meningeal niches. However, disruption of the blood-brain bather and inflammation can unleash stromal cells and trigger scar formation. Astroglia segregate from the inflammatory lesion core, and the so-called "glial scar" composed of hypertrophic astrocytes seals off the intact neural tissue from damage. In the lesion core, a second type of "fibrotic scar" develops, which is sensitive to inflammatory mediators. The fibrotic scar represents a major bather to CNS regeneration. Preventing of fibrosis may therefore prove to be a valuable therapeutic strategy for neurological disorders such as stroke, spinal cord injury and multiple sclerosis (see Fernández-Klett F, Priller J. The fibrotic scar in neurological disorders. Brain Pathol. 2014 July; 24 (4): 404-13).

By inhibiting glial scar formation around implantable neural, e.g. brain, electrodes according to the present invention, it is possible to use these devices for long term treatments and therapies, which is currently not possible.

Preferred is a neural implant according to the present invention, wherein said implant is permanent or non-permanent and is preferably selected from a measuring and/or stimulating electrode, such as flexible nanoelectrodes, a pacemaker, and a drug delivery device.

As described herein, the neural implant according to the present invention can be used, at least in part, as a drug delivery device. Thus, further preferred is a neural implant according to the present invention, wherein said biomaterial further comprises an active substance, which can be preferably selected from a pharmaceutically active drug, an antibiotic, a cytotoxic substance, an anti-inflammatory substance, a polypeptide, a polysaccharide, NGF, and collagen or other neurotropic and neuroprotective agents, such as, for example, BDNF.

Asplund et al. (Asplund M, Boehler C, Stieglitz T. Anti-inflammatory polymer electrodes for glial scar treatment: bringing the conceptual idea to future results. Front Neuroeng. 2014 May 13; 7:9) describe polymer electrodes that could also be useful as implants in the context of the present invention.

The inventors envisage our invention to lead to an improved therapeutic and also diagnostic use of brain electrodes and other neural (e.g. brain) implants. Especially, the use in deep brain stimulation of Parkinson's disease patients is envisioned. The inventors also envision biomaterials with the topography as described in the invention being inserted as a deliberate clinical intervention to disrupt existing glial scars, for example as an array of micron sized posts or pillars.

Another aspect of the present invention relates to a method for producing the neural implant according to the present invention as described herein, comprising the step of providing a prefabricated neural implant device with a biomaterial having an outer surface with a stochastic nanoroughness (Rq) of between 25 and 40 nm, preferably of between 32 nm+/−5 nm, and most preferred of about 32 nm. In the context of the present application, "about" shall mean+/−10 percent of a given value.

Preferred is a method according to the present invention, wherein said prefabricated neural implant device at least partially consists out of said biomaterial, or wherein said biomaterial is applied as a coating to said prefabricated neural implant device. The method can also comprise the prefabrication of the neural implant, including providing of the nanoroughness directly or indirectly (i.e. during production or as a separate production step) to the implant. Additionally/alternatively, in a preferred method according to the present invention, stochastic nanoroughness (Rq) is applied to said biomaterial using a suitable method known to the person of skill, preferably selected from polishing, machining, surface treatment, coating, cathodic polarization, acid etching, rolling, atmospheric plasma, laser treatment, and casting.

The present inventors envisage the invention to lead to an improved therapeutic and diagnostic use of brain electrodes and other brain implants. Especially, the use in deep brain stimulation of Parkinson's disease patients is possible. Thus, another aspect of the invention relates to the use of the neural implant according to the present invention for the diagnosis and/or treatment of a neurological disorder, such as, for example, Parkinson's disease, Alzheimer's disease, glioblastoma and/or for disrupting and/or preventing glial scars. Another aspect then relates to a method of diagnosing and/treating a neurological disorder, such as, for example, Parkinson's disease, Alzheimer's disease, glioblastoma and/or for disrupting and/or preventing glial scars, comprising the step of implanting a neural implant according to the present invention as described herein into a patient in need thereof. Preferably, the method also comprises a method of producing said implant as described herein, before implanting it.

In order to solve the above objects, in a second aspect of the present invention, the present inventors have furthermore found that nanoroughness can modulate the function of hippocampal neurons and its relationship with astrocytes. Blocking signaling via the mechanosensing cation channel Piezo-1 negated the ability of neurons to sense the nanoroughness and promoted decoupling of neurons from astrocytes (see Example 3, below, for siRNA knockdown).

The present invention includes the use of pharmacological inhibitors towards cell surface features that sense and respond to nanotopography, such as Piezo-1 Piezo-2 or other stretch activated ion channels that are influenced or impacted by nanotopography. Thus, inhibiting or interfering with them or knocking their expression down constitutes an important new therapeutic target and strategy.

The object of the present invention is thus further solved by an inhibitor of a mammalian mechanosensing ion channel of the family of PIEZO-1 and PIEZO-2 and/or other ion channels, such as TREK1, TRPC1 or TRPC6 (see, for example, Patel et al.; Pflugers Arch. 2010 August; 460 (3):571-81) for use in the diagnosis and/or treatment of a neurological disorder, such as, for example, Parkinson's disease, Alzheimer's disease, glioblastoma and/or for disrupting and/or preventing glial scars.

A mammal in the context of the present invention preferably is selected from a mouse, rat, monkey, goat, sheep, cat, dog, horse, rabbit, pig, and human.

As a preferred example and proof of concept, the inhibition of the mechanosensing ion channel Piezo-1, whose distribution is altered by nanotopography, was shown to abrogate the effects imposed by nanotopography and the association of neurons with astrocytes. Piezo-1 belongs to a mechanosensitive ion channel family with two mammalian members, PIEZO1 and PIEZO2 (Coste B, Mathur J, Schmidt M, Earley T J, Ranade S, Petrus M J, Dubin A E, Patapoutian A (October 2010). "Piezo1 and Piezo2 are essential components of distinct mechanically activated cation channels". Science 330 (6000): 55-60). Database Accession No. Q92508 describes the human piezo-type mechanosensitive ion channel component 1 (piezo 1), also named membrane protein induced by beta-amyloid treatment or FAM38A.

Brohawn et al. (Stephen G. Brohawn, Zhenwei Su, and Roderick MacKinnon Mechanosensitivity is mediated directly by the lipid membrane in TRAAK and TREK1 K+ channels. Proc Natl Acad Sci USA. 2014 Mar. 4; 111 (9):3614-9. Epub 2014 Feb. 18) show in cells that the K+ channel TRAAK (K2P4.1) is responsive to mechanical forces similar to the ion channel Piezo1, and that mechanical activation of TRAAK can electrically counter Piezo1 activation.

The finding that regions of amyloid plaque buildup in Alzheimer's involve changes to tissue nanoroughness provides a link between nanoscale physical cues and loss of function in neurons. Thus, in one preferred aspect thereof, the invention aims to inhibit neuronal death and loss of neuronal function in CNS neurons and thereby prevent the establishment and progression of Alzheimer's disease. Current drugs used for treating Alzheimer's disease only help to mask the symptoms but do not treat the underlying disease. These drugs work downstream of the deadly signaling cascade that is activated by dying cells in the CNS. The invention thus aims to stop or delay the cell damage that is mediated by amyloid-beta deposits and intracellular Tau tangles, and thereby improve the disease progression. In this invention the aim is to change the therapeutic paradigm for halting neuronal degenerative conditions, by changing the microenvironment of the neurons by targeting molecules expressed by astrocytes that can mediate and alter neuron function. This is different from current strategy targeting the beta amyloid deposits. Therefore, the discovery of Piezo-1 (and potentially other related cation channel proteins) present a new target to develop therapeutic agents and therapy against.

Thus, in another aspect thereof, the present invention relates to a method for identifying a modulator of the activity and/or expression of a mammalian mechanosensing ion channel selected from the family of PIEZO-1 and PIEZO-2 ion channels, comprising the steps of a) contacting a potential modulator of said mechanosensing ion channel with a cell expressing said mechanosensing ion channel, and b) identifying a modulator of said mechanosensing ion channel by detecting a change in the mechanosensing activity and/or expression of said ion channel in the presence of said modulator, compared to the absence of said modulator.

The term "contacting" in the present invention means any interaction between the potentially binding substance(s) with the mammalian mechanosensing ion channel as described herein, preferably selected from the family of PIEZO-1 and PIEZO-2 ion channels, whereby any of the two components can be independently of each other in a liquid phase, for example in solution, or in suspension or can be bound to a solid phase, for example, in the form of an essentially planar surface or in the form of particles, pearls or the like. In a preferred embodiment a multitude of different potentially binding substances are immobilized on a solid surface like, for example, on a compound library chip and the mammalian mechanosensing ion channel, preferably selected from the family of PIEZO-1 and PIEZO-2 ion channels (or a functional part thereof, such as PIEZO1) is subsequently contacted with such a chip. The protein employed in a method of the present invention can be a full-length protein or a fragment with N/C-terminal and/or internal deletions, as long as the protein or fragment thereof is still suitable for use in the method of the invention. Preferred is a method according to the present invention, wherein said change in the activity and/or expression is selected from a decrease or an increase of said mechanosensing activity and/or expression of said ion channel. More preferred is a decrease, for example using an siRNA (see example 3).

In the context of the present invention, the term "mammalian mechanosensing ion channel selected from the family of PIEZO-1 and PIEZO-2 ion channels" (herein also sometimes designated "ion channel") shall include the complete ion channel structure (e.g. FAM38) as well as subunits (e.g. the PIEZO-1 protein) or even functional parts thereof, as long these structures and/or elements can be used to screen for a modulator of the mechanosensing ion channel function in a cell. The person of skill is able to design and express suitable screening tools (see also below).

The potentially binding and/or modulating substance, whose change in the mechanosensing activity and/or expression of said ion channel is to be measured, can be any chemical substance or any mixture thereof. Preferred is a method according to the present invention, wherein the modulator is selected from the group consisting of a peptide library, a combinatory library, a cell extract, an aptamer (both oligonucleotides or peptides), a "small molecular drug", a polypeptide, such as, for example the toxin GsMTx4 or other suitable spider toxin venoms as described herein, an antibody or fragment thereof specifically binding to said mechanosensing ion channel, an antisense oligonucleotide, an siRNA, an mRNA, and a genetic deletion construct, preferably comprising a glial or neuronal cell-specific promoter. A particularly preferred modulator is one that can be used for gene-therapy in astrocytes. Also preferred is an ion-channel specific spider venom or active derivative thereof (see, for example, Kalia J, et al., From foe to friend: Using animal toxins to investigate ion channel function. J Mol Biol. 2014 Jul. 31. Yang S, et al., Effect of insecticidal fusion proteins containing spider toxins targeting sodium and calcium ion channels on pyrethroid-resistant strains of peach-potato aphid (*Myzus persicae*). Pest Manag Sci. 2014 Jul. 31).

Preferred is a method according to the present invention, wherein said mechanosensing ion channel is a cation ion channel, such as, for example, a sodium, calcium or potassium channel, such as, for example, a channel comprising human PIEZO-1 or human PIEZO-2, such as Mib or FAM38 or TRPC, such as TRPC1 or 6.

Further preferred is a method according to the present invention, wherein said detecting a change in the mechanosensing activity and/or expression of said ion channel in the presence of said modulator, compared to the absence of said modulator comprises a method selected from rtPCR, immunoprecipitation, blotting, voltage and patch clamping, electron spin resonance (ESR), atomic force microscopy (AFM), and/or a cell poking assay. All these assays are known in the state of the art.

Measuring of binding of the modulator to the ion channel can be carried out either by measuring a marker that can be attached either to the protein or to the potentially interacting compound. Suitable markers are known to someone of skill in the art and comprise, for example, fluorescence or radioactive markers. The binding of the two components can, however, also be measured by the change of an electrochemical parameter of the binding compound or of the protein, e.g. a change of the redox properties of the ion channel or the binding compound, upon binding. Suitable methods of detecting such changes comprise, for example, potentiometric methods. Further methods for detecting and/or measuring the binding of the two components to each other are known in the art and can without limitation also be used to measure the binding of the potential interacting compound to the ion channel or subunits or fragments thereof. The effect of the binding of the compound or the activity of the ion channel can also be measured indirectly, for example, by assaying an activity of the ion channel as described herein.

As a further step after measuring the binding of a potentially interacting/modulating compound and after having measured at least two different potentially interacting compounds at least one compound can be selected, for example, on grounds of the measured binding activity or on grounds of the detected increase or decrease of the ion channel (binding) activity and/or expression.

Further preferred is a method according to the present invention, further comprising testing said modulator as identified for its activity on the interactions of astrocytes with neurons, e.g., as described herein.

The thus selected binding compound is then in a preferred embodiment modified in a further step. Modification can be effected by a variety of methods known in the art, which include without limitation the introduction of novel side chains or the exchange of functional groups like, for example, introduction of halogens, in particular F, Cl or Br, the introduction of lower alkyl groups, preferably having one to five carbon atoms like, for example, methyl, ethyl, n-propyl, isopropyl, n-butyl, isobutyl, tert-butyl, n-pentyl or iso-pentyl groups, lower alkenyl groups, preferably having two to five carbon atoms, lower alkynyl groups, preferably having two to five carbon atoms or through the introduction of, for example, a group selected from the group consisting of $NH_2$, $NO_2$, OH, SH, NH, CN, aryl, heteroaryl, COH or COOH group.

The thus modified binding substances are than individually tested with a method of the present invention, i.e. they are contacted with the ion channel, and subsequently binding of the modified compounds to the ion channel is measured. In this step, both the binding per se can be measured and/or the effect on the expression function of the ion channel of the polypeptide can be measured. If needed the steps of selecting the binding compound, modifying the binding compound, contacting the binding compound with a polypeptide of the ion channel and measuring the binding of the modified compounds to the ion channel (and/or ion channel expressing cell) can be repeated a third or any given number of times as required. The above described method is also termed "directed evolution" since it involves a multitude of steps including modification and selection, whereby binding compounds are selected in an "evolutionary" process optimizing its capabilities with respect to a particular property, e.g. its binding activity, its ability to activate or modulate the activity of the ion channel.

In view of the above, possible applications of the present invention for humans include:

a) Diagnostic approaches: Since nanoroughness is linked with plaque formation, tests can be developed to assess an individual risk or the status in relation to Parkinson's disease, Alzheimer's disease or cancer based on the ion channel activity and/or expression, in particular in order to develop a personalized treatment plan.

b) Pharmaceutical and therapeutic approaches: The inventors' data indicate that an inhibition of the ion channel or the expression thereof can be used as preventing, treating and/or slowing down the course of Parkinson's disease, Alzheimer's disease or cancer in mammals/humans. An ion channel binding inhibitor/inhibiting genetic construct can be used as a drug as well.

Another aspect of the present invention then relates to a screening tool for identifying a modulator of the activity and/or expression of a mammalian mechanosensing ion channel selected from the family of PIEZO-1 and PIEZO-2 ion channels, comprising an isolated cell expressing a recombinant mammalian PIEZO-1 or PIEZO-2 protein, wherein said cell is not a human embryonic stem cell. The cell can be a prokaryotic or eukaryotic cell, and the expression constructs can be present extrachromosomally or integrated into the chromosome. The polypeptides can be expressed in the form of a fusion protein, for example together with an enzymatically active moiety as reporter-construct, in order to be able to detect the expression product. Preferred host cells are derived from cells selected from the brain, skeletal muscle, liver, adipose tissue, heart, pancreas, kidney, breast tissue, ovarian tissue, and/or hypothalamus. Preferred is a screening tool according to the present invention, wherein said cell is selected from the group of brain cells, recombinant host cells expressing the ion channel or a fragment or subunit thereof, yeast cells, and recombinant bacterial cells, wherein said recombinant cell optionally expresses the ion channel and/or a fragment or subunit thereof.

Preferred is thus a screening tool according to the present invention, wherein said cell is selected from the group of glial cells, neuronal cells, glioblastoma cells, recombinant mammalian host cells, yeast cells, and bacterial cells.

More preferred is a screening tool according to the present invention, wherein said recombinant mammalian PIEZO-1 or PIEZO-2 protein is labeled (see above).

According to yet another aspect thereof, the present invention relates to the use of the tools according to the present invention as described herein for screening for a compound that modulates the expression, the biological activity and/or the interaction of the ion channel in a cell as described herein.

Another aspect of the present invention relates to a method for manufacturing a pharmaceutical composition for treating or preventing a neurological disease (e.g. Parkinson's or Alzheimer's disease and/or brain cancer, comprising the steps of performing a method according to according to the present invention, and formulating said compound as identified into a pharmaceutical composition.

In a further embodiment of the method of the present invention, the interacting compound identified as outlined above, which may or may not have gone through additional rounds of modification, purification, and selection, is admixed with suitable auxiliary substances and/or additives. Such substances comprise pharmacological acceptable substances, which increase the stability, solubility, biocompatibility, or biological half-life of the interacting compound or comprise substances or materials, which have to be included for certain routes of application like, for example, intra cranial, intra spinal, intravenous solution, sprays, or pills. Carriers, excipients and strategies to formulate a pharmaceutical composition, for example to be administered systemically or topically, by any conventional route, in particular enterally, e.g. orally, e.g. in the form of tablets or capsules, parenterally, e.g. in the form of injectable solutions or suspensions, topically, e.g. in the form of lotions, gels, ointments or creams, or in nasal or a suppository form are well known to the person of skill and described in the respective literature. Administration of an agent, e.g., a compound can be accomplished by any method which allows the agent to reach the target cells. These methods include, e.g., injection, deposition, implantation, suppositories, oral ingestion, inhalation, topical administration, or any other method of administration where access to the target cells by the agent is obtained. Injections can be, e.g., intravenous, intradermal, subcutaneous, intramuscular or intraperitoneal. Implantation includes inserting implantable drug delivery systems, e.g., microspheres, hydrogels, polymeric reservoirs, cholesterol matrices, polymeric systems, e.g., matrix erosion and/or diffusion systems and non-polymeric systems, e.g., compressed, fused or partially fused pellets. Suppositories include glycerin suppositories. Oral ingestion doses can be enterically coated. Inhalation includes administering the agent with an aerosol in an inhalator, either alone or attached to a carrier that can be absorbed. The agent can be suspended in liquid, e.g., in dissolved or colloidal form. The liquid can be a solvent, partial solvent or non-solvent. In many cases, water or an organic liquid can be used.

Yet another aspect of the present invention is directed at a pharmaceutical composition for treating or preventing a neurological disease or brain cancer, obtained by a method according to the present invention.

Yet another aspect of the present invention is directed at a method for treating or preventing a neurological disease (e.g. Alzheimer's or Parkinson's disease or brain cancer in a patient, comprising administering to said patient an effective amount of a pharmaceutical composition according to the present invention.

In certain embodiments, the compound (inhibitor) is administered to the subject by administering a recombinant nucleic acid, such as, for example, an anti-PIEZO RNA, for example a siRNA. Preferably, the recombinant nucleic acid is a gene therapy vector. Preferred is a therapeutic method according to the present invention, wherein said mammal to be treated is a mouse, rat or human.

Preferably, an inhibiting active agent is administered in form of a pharmaceutical composition, such as an antibody, nucleotide or an inactivating binding compound for the ion channel function. Preferably, said patient is a human being. Treating is meant to include, e.g., preventing, treating, reducing the symptoms of, or curing the disease or condition, i.e. the neuronal disease and/or cancer.

An "effective amount" is an amount of the compound(s) or the pharmaceutical composition as described herein that reduces on the expression and/or abundance of the ion channel, or inhibits and/or reduces the activity of the ion channel. The amount alleviates symptoms as found for neuronal diseases and/or cancer. Alleviating is meant to include, e.g., preventing, treating, reducing the symptoms of, or curing the disease (Parkinson's or Alzheimer's disease, glial scar, and/or cancer) or condition (e.g. tumor size and/or metastases or plaque formation).

Preferred is a method according to the present invention, wherein said neurological disease or brain cancer is selected from Alzheimer's disease, Parkinson's disease, glial scar, and glioblastoma, such as glioblastoma multiforme.

The invention also includes a method for treating a subject at risk for a neuronal disease or cancer, wherein a therapeutically effective amount of a modulator as above is provided. Being at risk for the disease can result from, e.g., a family history of the disease, a genotype which predisposes to the disease, or phenotypic symptoms which predispose to the disease. A further aspect of the present invention is the use of a modulator of the expression and/or the biological activity of the ion channel for the manufacture of a pharmaceutical composition for treating or preventing a neuronal disease and/or cancer. Preferably, said modulator is an inhibitor of the expression and/or biological activity of the ion channel as described herein.

By treating the underlying cause for neuronal cell death in Alzheimer's brains, we aim to improve, stop or delay the disease progression, as it is not possible thus far. The inventors envisage the invention to lead to an improved therapy of patients with Alzheimer's disease, and that this discovery also applies to a treatment of glioblastoma multiforme (GBM), a fatal form of brain cancer, which is caused by uncontrolled proliferation of astrocytes. GBM currently has only very few treatment options.

Another aspect of the present invention then relates to a monoclonal antibody or a functional fragment thereof (such as, for example, an scFv or Fab fragment) that specifically recognizes and interacts with the mechanosensitive function of the ion channel, e.g. PIEZO1 or 2. Preferably, said monoclonal antibody or a functional fragment thereof interferes (such as inhibits) the formation of the ion channel. The antibodies or fragments thereof can also be labeled, and/or carry a therapeutic group attached to them (as described above).

In sum, the key findings of the present invention provide evidence for the hitherto unexplored role for ECM and glial cell associated changes to stochastic nanoroughness in neurodevelopment and neuropathologies. These new insights prove valuable in the development of new therapeutic targets and design principles for engineering materials and interfaces for neural interfacing.

The present invention will now be described further in the following examples with reference to the accompanying figures, nevertheless, without being limited thereto.

In the Figures:

FIG. 1 shows a panel of the formation of glial scar tissue in vitro on a smooth glass surface (top panel; Rq=3.5 nm). In comparison, no glial scar tissue is formed on surfaces with a modified topography (bottom panel; Rq=32 nm). Rq is the root mean square roughness.

FIG. 2 shows (left) the relative amount of glial scar tissue formed in vitro around polymer wires (grey bar) or coated polymer wires with an altered surface topography (black bar). The right figure shows the size of glial scar tissue formed in vitro after re-plating onto plain glass which is a smooth surface (black line) or surfaces with a modified topography, Rq 32 nm (grey line).

FIG. 3 shows the morphological and functional traits in PC-12 cells on nanorough substrates: (a) Atomic force microscopy (AFM) of silica nanoparticle (SNP) modified substrates with the corresponding surface roughness Rq. (b) Morphology of PC-12 cells on Rq=3.5 nm, Rq=32 nm and Rq=80 nm visualized by staining for F-actin. Impact of nanoroughness on PC-12 polarization as assessed by determining: (c) number of neurites per cell and (d) neurite length. (e) Influence of nanoroughness on acetylcholinesterase (AChE) activity. Calcium sensitive FURA-2 imaging of differentiated PC-12 cells on smooth glass substrates and surfaces with an Rq of 32 nm: (f) change in intracellular calcium levels as assessed by FURA-2 intensity, (g) rate of depolarization as determined by the slope of the depolarization portion of the curve (immediately after addition of KCl). Statistical significance: *$p<0.05$; $p<0.01$; *$p<0.001$.

FIG. 4 shows that the morphology and function of rat hippocampal neurons and astrocytes are influenced by substrate roughnesses: Neuron-astrocyte interaction on (a) smooth glass substrate, (b) on substrate of Rq=32 nm. Astrocytes were visualized using antibody against GFAP (dark gray) and neurons were visualized using antibody against MAP-2 (light gray). Quantification of neuron-astrocyte association in: (c) short-term cultures (5 days), and (d) long-term cultures (6 weeks). Calcium sensitive FURA-2 imaging in hippocampal neurons on smooth glass substrates and surfaces with Rq of 32 nm: (e) change in intracellular calcium level as assessed by FURA-2 intensity, (f) rate of depolarization as determined by the slope of the depolarization portion of the curve (immediately after addition of KCl). Statistical significance: ***$p<0.001$.

FIG. 5 shows that piezo-1 is necessary for sensing nanotopography: (a) Representative scanning electron micrograph of PC-12 cells grown on nanorough surface (shown Rq=40 nm). PC-12 stained using anti-FAM38A, an antibody for Piezo-1 mechanosensitive ion channel on Rq=3.5 nm (b) and Rq=32 nm (c). On smooth surfaces, FAM38A staining is pronounced at neurite branch points (denoted by circles) (b), while on nanorough surfaces FAM38A staining is uniform along all neurite processes (c). Rat dorsal root ganglia morphology (d, e) and function (f, g) on glass and Rq of 32 nm. Inhibition of FAM38A with GsMTx4 (5 µM) results in decoupling of hippocampal neurons from astrocytes on smooth glass substrates (h, i). The FURA-2 intensity profile (j), and rate of calcium influx (k) in hippocampal neurons upon depolarization with KCl on smooth glass substrate and Rq=32 nm is identical upon inhibition of FAM38A. Statistical significance: ***$p<0.001$.

FIG. 6 shows that nanoroughness alters physical attributes of astrocytes: Dependency of astrocyte form factor on substrate nanoroughness: (a) Decrease in form factor on 32 nm Rq surfaces is consistent with a more motile phenotype (inset). Morphological changes to astrocyte cell surface on nanorough surfaces: AFM images of astrocytes grown on glass (b) and on Rq=32 nm (c) and the corresponding transverse line scans, and changes to topography of astrocyte surface on 32 nm surfaces (d). Shaded areas show representative areas for Rq calculations. Amyloid-beta plaques are associated with topographical changes to brain tissue: Paraffin embedded human brain slices stained with Bielschowsky's silver stain (e): Left image; healthy human (AD−), Right image; patient diagnosed with Alzheimer's (AD+): revealing amyloid β plaques indicated by yellow arrowheads. Bottom panel; tapping mode AFM scans (10 µm×10 µm) of one of the representative areas (top), higher magnification (2 µm×2 µm) scan of the same area (bottom), and transverse views of the corresponding 2 µm×2 µm image above. (f) Histograms of Rq values of healthy brain tissue, and amyloid-β plaques in Alzheimer's patients showing a general shift of tissue roughness to higher Rq's and an increased heterogeneity in roughness in AD+ brain slices. Rq values were calculated using a 700 nm×700 nm scan area.

Figure 14:
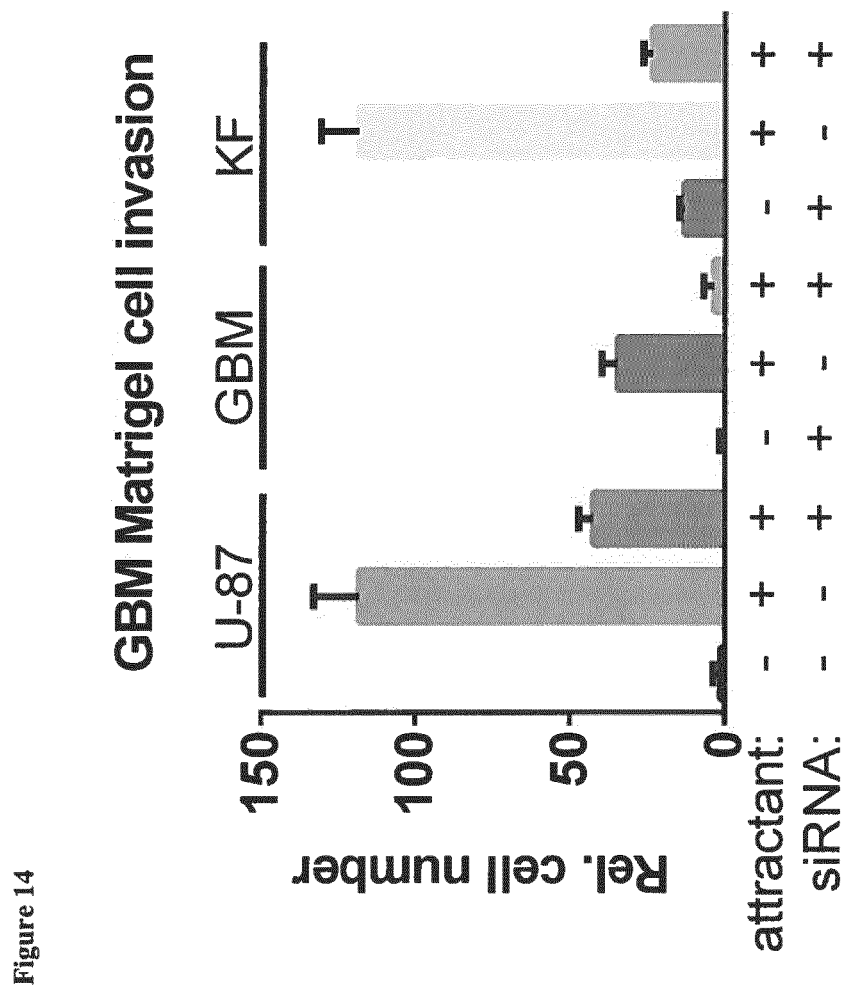

FIG. 14 shows that using glioblastoma multiforme (GBM) cell lines and primary GBM cells from human tumor explants, their migration in a trans well migration assay can be completely stopped by knocking down piezo-1. GBM=GBM-1; KF=GBM-2.

EXAMPLES

Example 1

Figure 1:
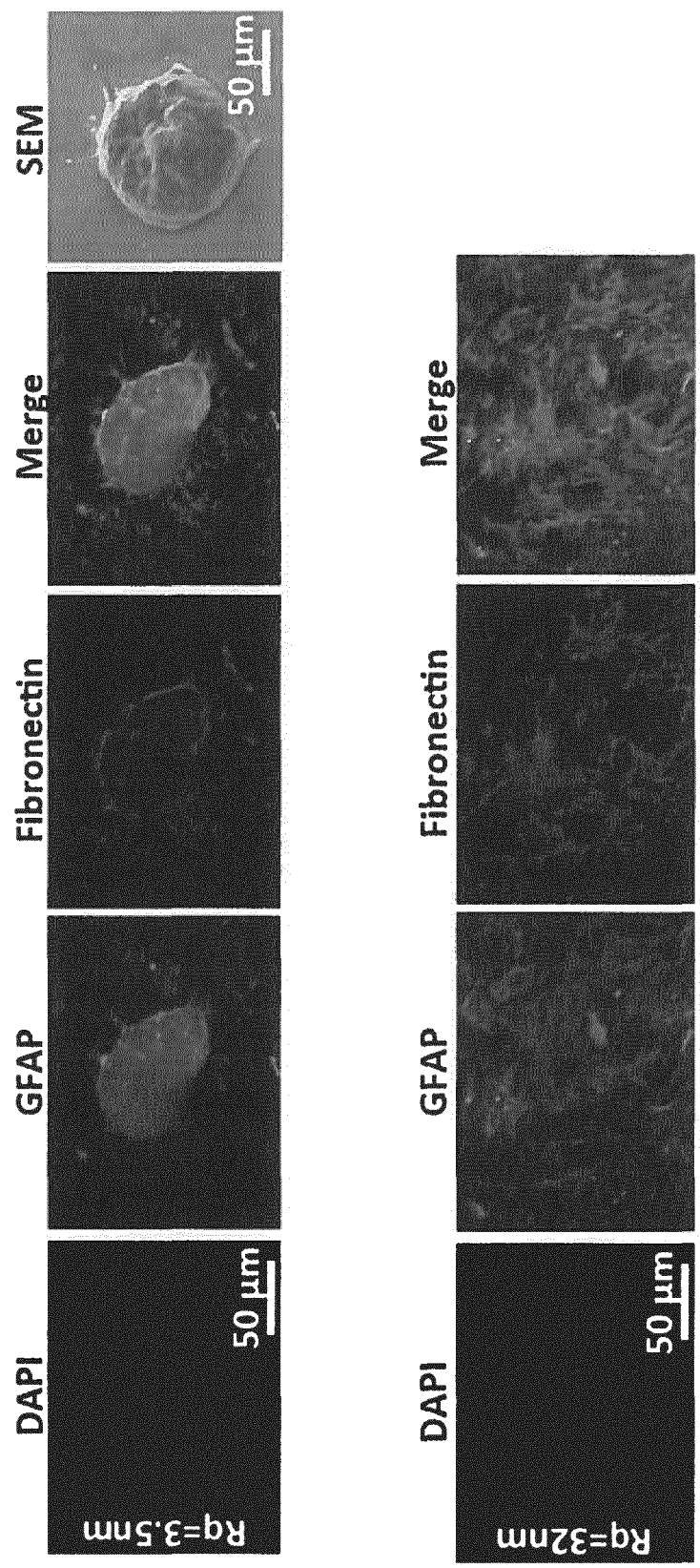
Figure 2:
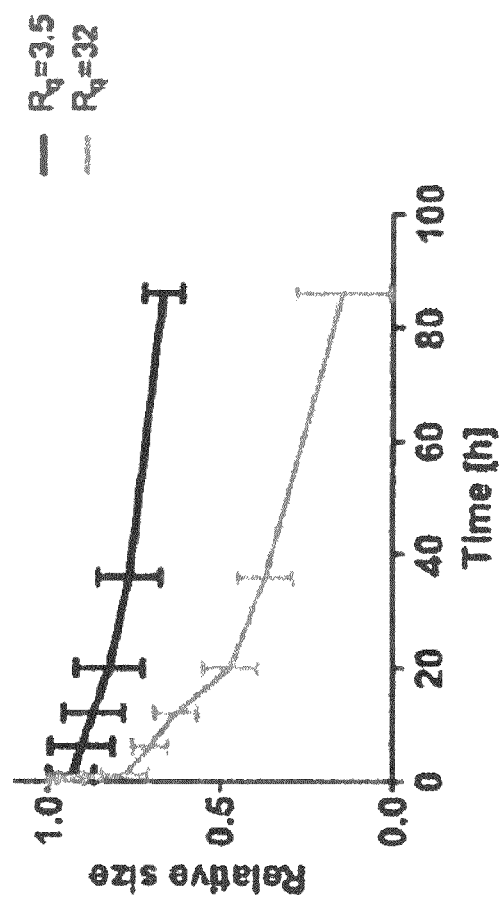
Figure 2:
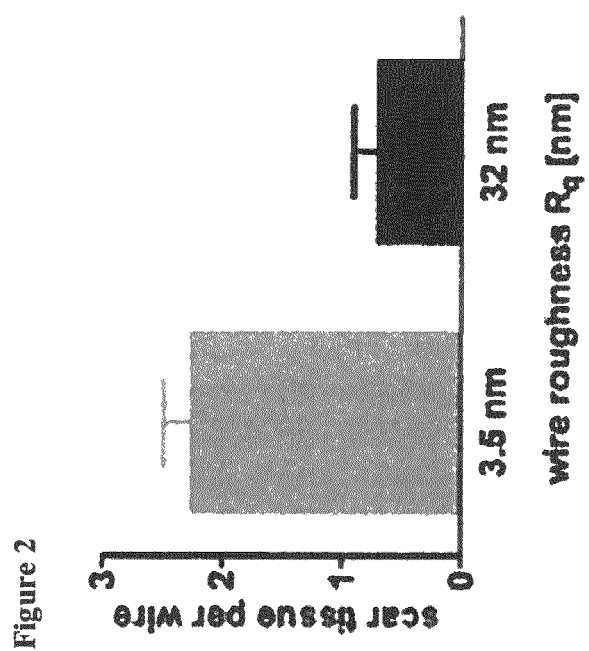

The properties of the inventive biomaterial surface were tested and verified in a clinically relevant experimental model. In the in vitro model of glial scarring, polymer wires with the surface coating were able to inhibit glial scar formation. Moreover, already (in vitro) formed glial scar tissue decomposed when exposed to a specific regimen of nanotopography as it is used for the coating. Polymer wires with surface coating were implanted into Agarose gels with an almost similar consistency as brain tissue, and the coating was shown to be stable after this implantation (see FIGS. 1 and 2).

The surfaces of the materials can be characterized for morphology and roughness using scanning electron microscopy (SEM).

Example 2

Nanotopography Modulates PC-12 Cell Polarity and Enhances Function

Figure 3:
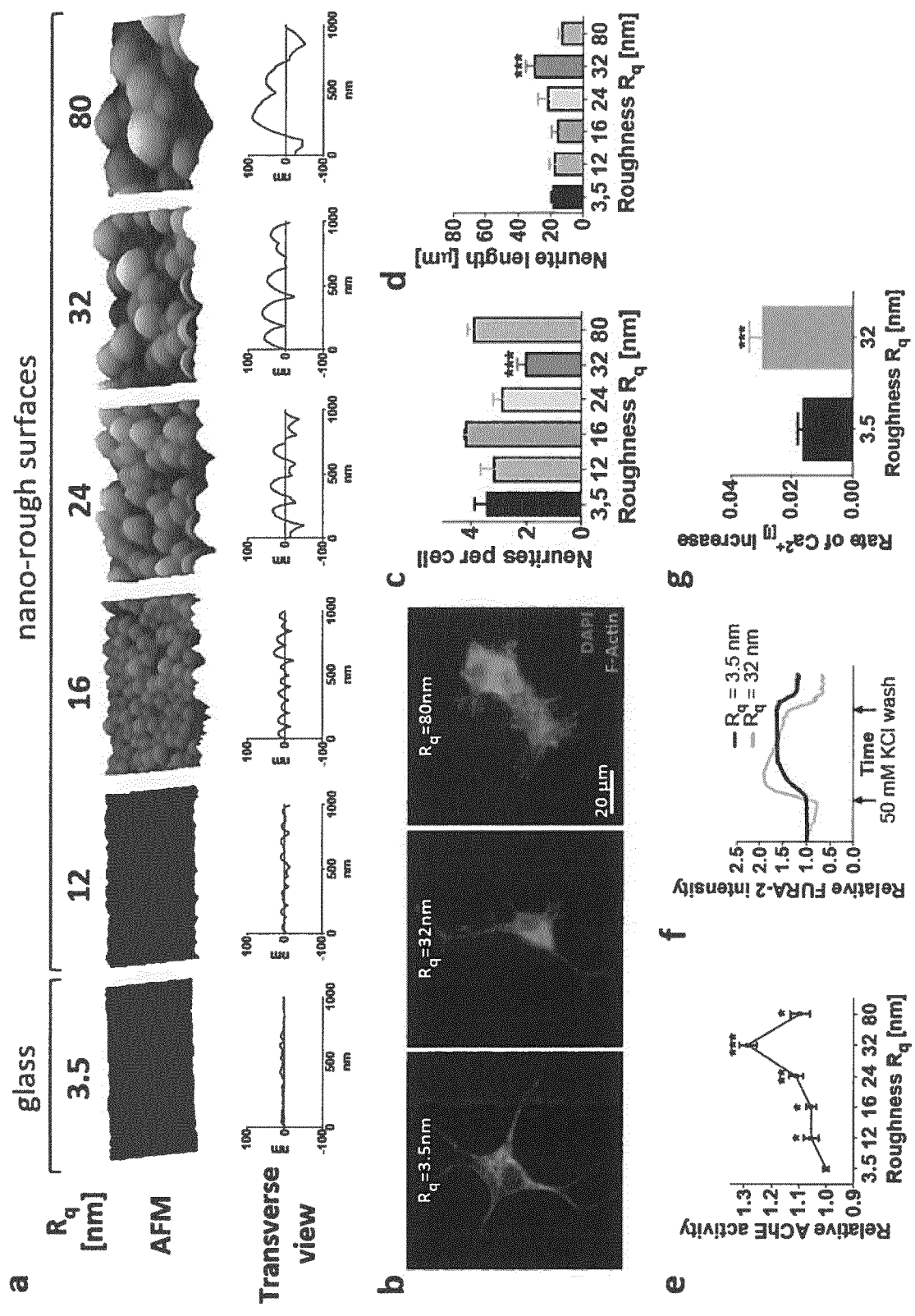

Since macromolecules are in a state of high entropy, and entropy is a statistical measure of randomness, the roughness presented by macromolecules is expected to be stochastic (random). The inventors simulated random ECM nanoroughness using an assembly of monodispersed silica colloids of increasing size (Lipski A M, Pino C J, Haselton F R, Chen I-W, Shastri V P (2008) The effect of silica nanoparticle-modified surfaces on cell morphology, cytoskeletal organization and function. *Biomaterials* 29:3836-46, Lipski a. M et al. (2007) Nanoscale Engineering of Biomaterial Surfaces. *Adv Mater* 19:553-557) (FIG. 3a). The roughness in this system scales logarithmically with nanoparticles radius and can recapitulate topography from the level of receptor clusters to ECM features (Shastri V P (2009) In vivo engineering of tissues: Biological considerations, challenges, strategies, and future directions. *Adv Mater* 21:3246-54), and further allows the production of surfaces with stochastic nanoroughness. In contrast, surfaces consisting of periodic groves and ridges that have been extensively studied present deterministic roughness.

As a first step, the inventors investigated the ability of PC-12 cells (Greene L, Tischler S (1976) Establishment of a noradrenergic clonal line of rat adrenal pheochromocytoma cells which respond to nerve growth factor. *Proc Natl Acad Sci USA* 73:2424-8), a well-established model system for studying neuronal differentiation, to perceive stochastic nanoroughness and analyzed changes to their morphology and function.

PC12 cells are indeed able to perceive the underlying nanoroughness (in an NGF- and collagen-dependent manner) and showed an increased differentiation and associated functional traits on a specific Rq of about 32 nm as evident from a highly polarized cell morphology (FIG. 3b, middle panel) and associated changes such as fewer and longer neurite outgrowths (FIGS. 3c and 3d) compared to glass, which is considered a smooth substrate (Rq approx. 3.5 nm, FIG. 3b, left panel). Beyond this optimal substrate roughness, cells were more prone to clumping (FIG. 3b, right panel). If the slides or culture substrates is not coated with collagen, then the PC-12 cells cannot sense the roughness, and also they need NGF in order to express neurites which are the sensing elements for sensing the nanotopography. For growing neuronal cells, in general one has to coat the substrate with either collagen polylysine or other polycation, such as poly-L-ornithine. Nevertheless, this coating does not affect the roughness and/or Rq values.

One measure of the functional state of a neuron is the activity of acetylcholinesterase (AChE) as this is necessary for synaptic communication. Interestingly, AChE levels also peaked in PC-12 cells on 32 nm Rq surfaces (FIG. 3e), which also coincided with an accelerated and elevated calcium response to depolarization (FIGS. 3f and 3g).

Nanotopography Mediates Hippocampal Neuron-Astrocyte Interaction

The inventors then posed the following question: can neuronal cells in general perceive nanoroughness and, if so, does it have a role in defining their interaction and function? Hippocampal neurons are responsible for memory formation. Loss of their function and death has been linked to neuropathologies, such as Parkinson's and Alzheimer's disease.

The inventors therefore evaluated the response of mixed primary cultures of rat hippocampal neurons and astrocytes to the different roughness regimes. Surprisingly, primary hippocampal neurons also responded to roughness in a manner similar to dopaminergic PC-12, and exhibited prominent, axon like polarized structures on exactly the same Rq of 32 nm.

Figure 4:
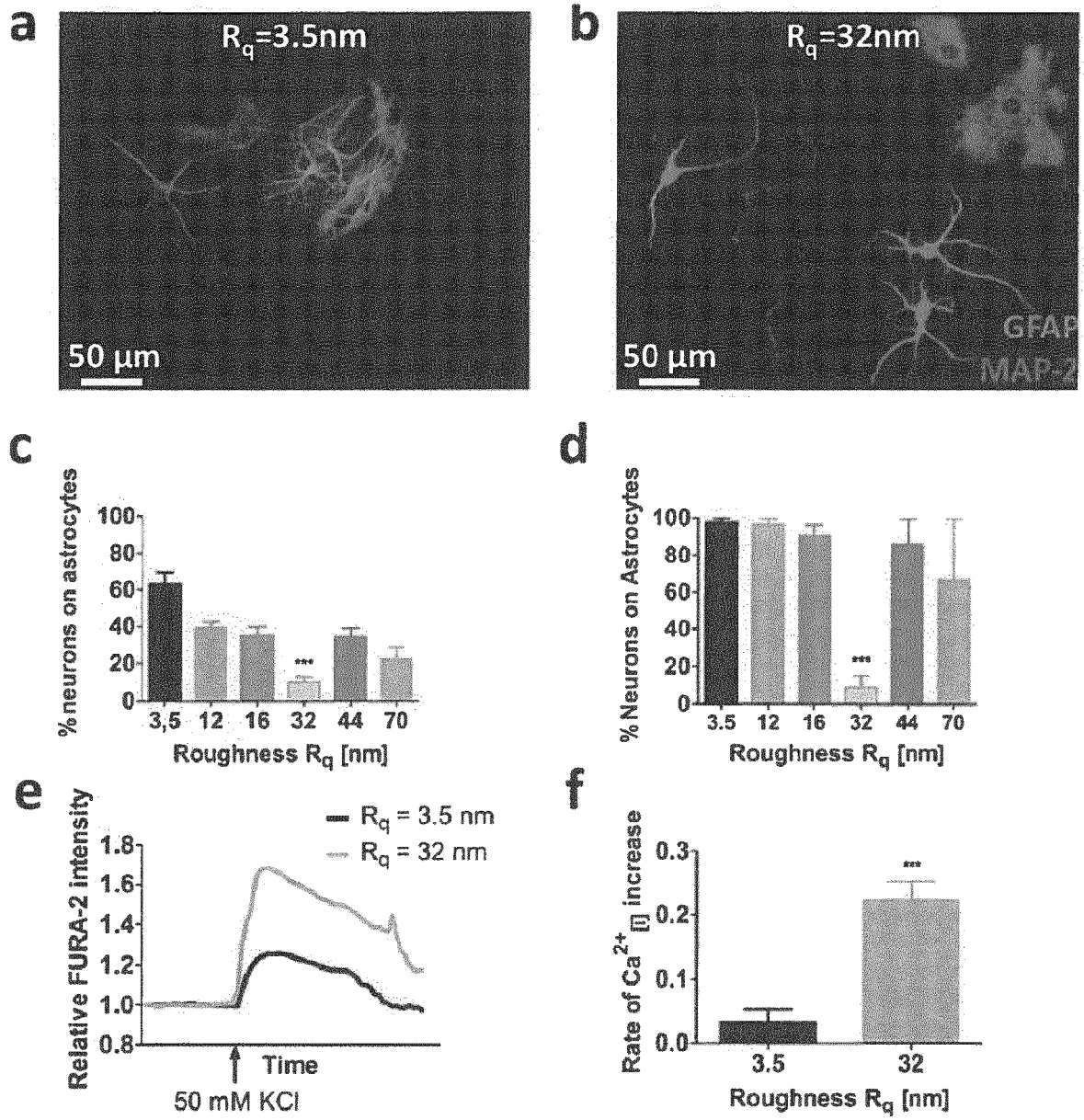

An also remarkable finding was that nanoroughness appeared to modulate the relationship, and dependency of neurons on astrocytes. It is well established that neurons require astrocytes for survival (Cui W, Allen N D, Skynner M, Gusterson B, Clark a J (2001) Inducible ablation of astrocytes shows that these cells are required for neuronal survival in the adult brain. *Glia* 34:272-82), and indeed, on surfaces with an Rq above and below 32 nm, neurons were predominantly found associated with astrocytes (FIGS. 4a and 4c). However, on Rq of approx. 32 nm, neurons were dissociated from astrocytes (FIGS. 4b and 4c) and continued to survive independently even up to 6 weeks (FIG. 4d). After 5 days, the percent neurons that were associated with astrocytes on the 32 nm Rq surface was around 15%, which was 1.5-2 fold lower than those on other Rq's, which ranged from 20-40%, and 6 fold lower than that on the smooth glass substrate (FIG. 4c). That is, in comparison to the other Rq's, over twice as many neurons on 32 nm Rq surface were surviving independently of astrocytes. At 6 weeks however, the percent of neurons that were surviving independently of astrocytes on the 32 nm Rq was over 6 fold greater in comparison to the other Rq's. While over 90% of neurons were associated with astrocytes on other roughnesses, only 15% of neurons were associated with astrocytes on 32 nm Rq (FIG. 4d). Remarkably, hippocampal neurons on 32 nm Rq surfaces in spite of being dissociated from astrocytes showed an order of magnitude faster and stronger increase in intracellular calcium levels following membrane depolarization in comparison to those on smooth surfaces (FIGS. 4e and 4f). Thus, there seemed to be a favorable Rq of around 32 nm at which both PC-12 and hippocampal neurons appeared to be more functional.

Mechanosensing Ion Channel—Piezo-1 is Responsible for the Sensing of Nanoscale Physical Cues by Neurons Past studies showed that stochastic nanoroughness altered the organization of focal adhesion complexes in highly migratory preosteoblasts and endothelial cells (A M Lipski, C Pino, F R Haselton, I-W. Chen, and V P Shastri; "The effect of silica nanoparticle-modified surfaces on cell morphology, cytoskeletal organization and function", Biomaterials, (28), 3836 (2008)). Since neurons have limited migratory capacity (Fricker R a et al. (1999) Site-specific migration and neuronal differentiation of human neural progenitor cells after transplantation in the adult rat brain. *J Neurosci* 19:5990-6005), a critical open question was how neurons perceive nanoroughness. Scanning electron micrographs revealed that the neurites indeed make intimate contact with the underlying topography (FIG. 5a). Such intimate contact between the neurites and the surface ought to manifest itself as changes in membrane tension. Since the conformation and distribution of mechanosensitive ion channels is altered in response to changes in membrane tension and curvature (Nilius B (2010) Pressing and squeezing with Piezos. *EMBO Rep* 11:902-3), the inventors investigated the expression pattern of FAM38A, an integrin-activated transmembrane protein, which is part of the mechanosensitive ion channel Piezo-1 (Coste B et al. (2010) Piezo1 and Piezo2 are essential components of distinct mechanically activated cation channels. *Science* 330:55-60). Piezo-1 is expressed by CNS neurons and not by sensory neurons like dorsal root ganglia (DRG) (Roudaut Y et al. (2012) Touch sense: functional organization and molecular determinants of mechanosensitive receptors. *Channels* 6:234-45).

It was observed that, while FAM38A expression in PC-12 cells on glass was predominantly localized at neurite branchpoints which would be a region of high cytoskeletal tension (FIG. 5b), in contrast, a more uniform distribution of FAM38A could be seen on the optimal Rq of 32 nm, suggesting a dramatic change to the mechanical environment of the neurite as they perceive the nanoroughness (FIG. 5c). Since FAM38A expression level was not altered, and PC-12 during differentiation did not show any changes in attachment force or motility in response to nanoroughness, the observed changes to Piezo-1 expression pattern can be linked to the underlying nanotopography.

The role of Piezo-1 in sensing topography is further bolstered by the findings that DRGs, which lack this mechanosensitive channel, but possess Piezo-2 instead, do not show any morphological changes on nanoroughness substrates (FIGS. 5d and 5e). This is further confirmed by imaging the calcium flux, which showed similar depolarization patterns and rate of calcium influx in DRGs grown on Rq of 3.5 and DRGs grown on Rq of 32 nm (FIGS. 5f and 5g).

Neuron-Astrocyte Interactions Involve Topographical Cues Provided by Astrocytes and Piezo-1

As indicated above, primary hippocampal neurons require the interaction with astrocytes for their survival (Cui W, Allen N D, Skynner M, Gusterson B, Clark a J (2001) Inducible ablation of astrocytes shows that these cells are required for neuronal survival in the adult brain. *Glia* 34:272-82). This raised the question as to why do the neurons favor the surface over association with the astrocytes. AFM analysis of the surface of astrocytes associated with neurons led the inventors to the remarkable finding that the roughness of the astrocyte surface was around an Rq of 26-28 nm (FIG. 6d), and this coincides rather well with the roughness regime on which neurons exhibit decoupling from astrocytes.

A role of mechanotransduction in maintaining neuron-astrocyte interactions is further supported by the inventors' findings that upon inhibition of Piezo-1 with the toxin GsMTx4 (Delmas P, Hao J, Rodat-Despoix L (2011) Molecular mechanisms of mechanotransduction in mammalian sensory neurons. *Nat Rev Neurosci* 12:139-53, Bae C, Sachs F, Gottlieb P (2011) The mechanosensitive ion channel Piezo1 is inhibited by the peptide GsMTx4. *Biochemistry* 50:6295-6300), neurons decouple from astrocytes even on smooth glass substrates (FIGS. 5h and 5i) where their normally show strong association (FIGS. 4a, 4c, and 4d). Furthermore, the increased sensitivity to depolarization that was observed in hippocampal neurons on Rq of 32 nm is lost upon inhibition of Piezo-1 (FIGS. 5j and 5k). This provides direct evidence for the role of nanotopography is influencing hippocampal neuron-astrocyte interaction and function through mechanotransduction, and a clear role for stretch-activate ion channels in these processes.

Regions of Amyloid Plaque Build-Up in Alzheimer's Present Increased Tissue Nanoroughness The inventors' observation that topography of astrocytes, a support cell for neurons, can dictate the function of the phenotypically unrelated neurons, points to a larger paradigm wherein physical and mechanical information provided by astrocytes and ECM macromolecules play a role not only in neuronal development but also in neuropathologies. There is ample evidence that the loss of memory associated with Alzheimer's disease (AD) is due to the death of hippocampal neurons. PGs like chondroitin sulfate PGS (CSPGs) have been implicated both in neural differentiation and neuropathologies such as Alzheimer's (Galtrey C M, Fawcett J W (2007) The role of chondroitin sulfate proteoglycans in regeneration and plasticity in the central nervous system. *Brain Res Rev* 54:1-18). CSPGs have been found to co-localize with amyloid-β plaques, and in vitro studies have shown that CSPGs can promote amyloid-β fibril assembly a key step in plaque formation. Interestingly, amyloid-β stimulates CSPG production in astrocytes, which has negative effects on neuronal health and synapse formation.

Figure 6:
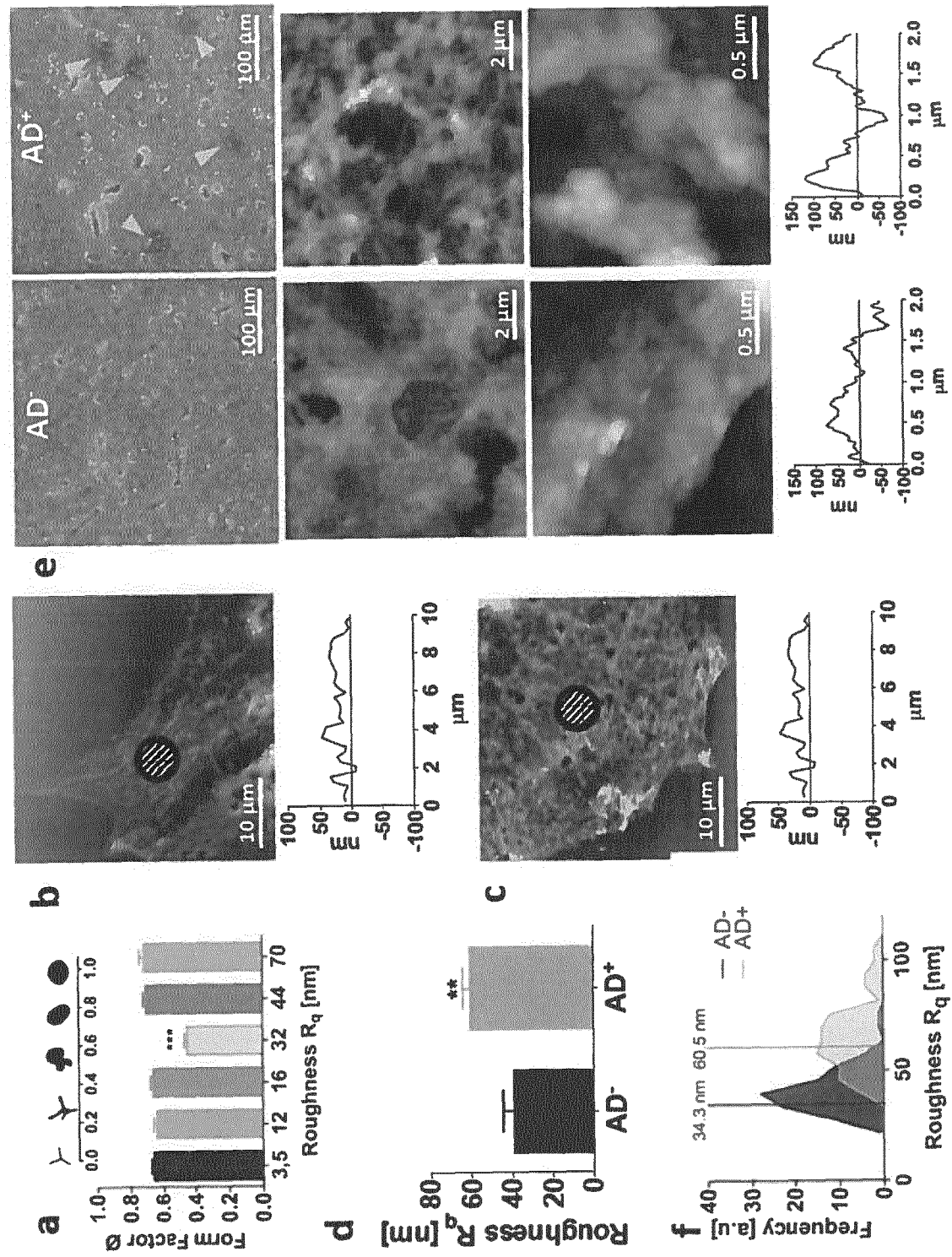

Thus, the loss of hippocampal neuron function in Alzheimer's seems to be triggered by changes to the topography that the neurons experience. In order to investigate this premise further, the inventors analyzed the topographical characteristics of amyloid-β plaques in the hippocampus of human brain slices using AFM (FIG. 6e). The inventors made the compelling observation that while the Rq of healthy brain tissue (AD−) showed a Gaussian distribution with a median centered around 34 nm, the tissue of individuals diagnosed with Alzheimer's (AD+) showed a bimodal distribution of tissue roughness with a pronounced shift in the median towards higher Rq values of 60 nm accompanied by a more heterogeneous Rq pattern (FIG. 6f). The emergence of Rq values greater than 80 nm, which is the range of Rq where the inventors observe increased neuronal cell death, is in accordance with published reports that neurons, when exposed to amyloid-β undergo apoptosis (Fraser P E, Lévesque L, McLachlan D R (1994) Alzheimer A beta amyloid forms an inhibitory neuronal substrate. *J Neurochem* 62:1227-30; Ivins K J, Thornton P L, Rohn T T, Cotman C W (1999) Neuronal apoptosis induced by beta-amyloid is mediated by caspase-8. *Neurobiol Dis* 6:440-9). The current observation that astrocyte shape is affected by nanoroughness provides evidence that cell signaling in the neuronal environment may be additionally mediated by ECM-based cues.

The effects of stochastic nanoroughness on neuronal health seem to manifest itself in two possible scenarios: (1) The changes to tissue roughness affects glial cell behavior which then instigates changes to neuron signaling environment, and/or (2) the changes to generally stationary cells that provide a supportive network for neuronal cells and synapses, migratory and proliferating astrocytes have been observed in glial scarring, an environment with diminish neuronal function (Buffo A, Rolando C, Ceruti S (2010) Astrocytes in the damaged brain: molecular and cellular insights into their reactive response and healing potential. *Biochem Pharmacol* 79:77-89, Wanner I B et al. (2013) Glial scar borders are formed by newly proliferated, elongated astrocytes that interact to corral inflammatory and fibrotic cells via STAT3-dependent mechanisms after spinal cord injury. *J Neurosci* 33:12870-86). In the present invention, an altered cellular environment in the form of nanotopography was shown to affect astrocyte biophysical attributes (shape, roughness) so as to alter its interaction with neurons.

Strong evidence for the second scenario is derived from a recent study by Satoh et al. (Satoh K et al. (2006) A novel membrane protein, encoded by the gene covering KIAA0233, is transcriptionally induced in senile plaque-associated astrocytes. *Brain Res* 1108:19-27), showed that hMib (a human ortholog of rodent Piezo-1) is transcriptionally induced in activated astrocytes associated with senile amyloid-β plaques in AD+ human brains. Interestingly, neurons that express hMib show damaged morphology while healthy looking neurons do not express hMib. The ability to sense the changes to astrocyte topography induced by tissue roughness seems to have triggered undesirable changes in hMib+ neurons. Conversely, the inability to sense the mechanical cues provided by the astrocytes seems to play a role in the loss of function in the hMib− neurons. Since healthy neurons are hMib+, loss of this marker seems to additionally play a role in the functional deficiency associated with Alzheimer's.

Example 3

Piezo-1 Knockdown Using siRNA

Scanning electron microscopy: For imaging cells grown on nanoparticle modified surfaces, cells were fixed in 4% PFA for 30 minutes, washed with PBS and dehydrated in an increasing ethanol gradient followed by a drying phase in vacuum. Imaging was accomplished with a Quanta 250 FEG (FEI Inc.) equipped with the FEIxT software.

Atomic force microscopy: Scans were done in tapping mode with a Dimension V atomic force microscope (Bruker Ltd.) equipped with the Nanoscope software (V.7.3, Bruker Ltd.). Nanoparticle modified surfaces and Alzheimer's disease (AD) samples were measured with a phosphorus-doped silica cantilever in air (k=3 N/m, $f_0$=74-90 kHz) at a scan rate of 0.9 Hz with 256 lines per image. Per batch of coated SNPs, three different substrates were analyzed and the root mean square roughness $R_q$ calculated for three independent regions of each substrate. Amyloid-β plaque roughness was determined for a total of 100 areas (from two individual patients per condition) positively stained in the silver staining (as described see below).

Cells were fixed in 4% PFA for 30 minutes, washed with PBS and imaged in water with the help of a fluid cell. Scan were done with a silicone tip on nitride lever (k=0.32 N/m, $f_0$=40-75 kHz) at 512 lines per image with a scan rate of 0.312 Hz. For astrocyte cell surface roughness measurements, 15 cells from 3 different animals were measured. For $R_q$ calculations of the cell surface, a total of 150 areas were analyzed.

Immunocytochemistry: Cells were fixed for 30 minutes with 4% paraformaldehyde before antibody specific staining. Postmitotic neurons were visualized with an anti-MAP-2 antibody (Abcam), early stage neurons with an anti-neuron specific class III β-tubulin antibody (TuJ-1, Abcam) and astrocytes with an anti-GFAP antibody (Dako GmbH). The stretch activated ion channel Piezo-1 was identified with an anti-FAM38A antibody (Abcam Inc.). Visualization of the actin cytoskeleton was done with phalotoxin conjugated to Alexa Fluor488 (Invitrogen Life Technologies GmbH, Germany).

Cell density/composition analysis: In order to analyze the cell density and composition of mixed neuron/astrocyte cultures on the different substrates at the end of the experiments, MAP-2$^+$, GFAP$^+$ and Tuj-1$^+$ cells were counted in 4 separately isolated cultures in 10 random image sections and on two different substrates of each isolated culture.

Morphological analysis: Morphological changes in cells grown on SNP modified substrates were analyzed in biological and technical triplicates. Per condition and substrate 20 random pictures were used for evaluation of morphological changes. For PC12 cells, only those not contacting other cells, and only processes extending from the cell soma with a length bigger than the cell's diameter were used for analysis. The astrocyte form factor was analyzed with the help of ImageJ (Fiji V.1.47p, NIH, USA) and calculated according to the following formula:

$$\phi = \frac{4\pi A}{p^2}$$

Where, A is the cell's diameter and p the cell's perimeter. Values for the form factor can be between zero and one, zero almost being a line and one being a perfect circle.

Small interfering RNA knockdown experiment: For all transfection experiments, primary hippocampal neuron/astrocyte cultures were seeded as 7.5*10$^4$ cells/cm$^2$ and cultured in serum containing media. Rat FAM38A small interfering RNA (On-Target Plus, Dharmacon), control small interfering RNA (AllStars negative siRNA, Qiagen) and/or the transfection reagent DharmaFect 3 (Dharmacon) was added to the culture in varying concentrations after 24 h in serum free Neurobasal media supplemented with B27 and glutamine and according to the manufacturer's instructions. The siRNA sequences targeting FAM38A were the following:

```
                                    (SEQ ID No: 1)
    5'-GCACAAAGGCCUCCGACUU-3', (SEQ ID No: 2)
    5'-GGGUUGAAGAUUCGGGAGA-3', (SEQ ID No: 3)
    5'-CGGAAGAAUGGCAGCGCAU-3',
    and (SEQ ID No: 4)
    5'-CAGAUGAACAGUUGGGCGA-3'.
```

Knockdown efficiency was assessed by quantitative real-time PCR.

Calcium sensitive imaging: Intracellular calcium levels were measured with the cell permeable probe FURA-2-acetoxymethyl ester (Invitrogen Life Technologies GmbH). Cells were exposed to 5 μM FURA-2-AMin DMSO (final concentration of 0.2%) for 45 minutes in a humidified incubator at 37° C. Increase in intracellular calcium levels following depolarization with 50 mM KCl was analyzed by the change in the absorption and emission spectra of FURA-2 upon Ca$^{2+}$ binding using a custom-built perfusion chamber mounted to a Zeiss Observer Z1 and the ZEN blue software (Zeiss AG, Germany). The rate of intracellular Ca$^{2+}$ increase was calculated as the slope of the linear portion of the increase in FURA-2 intensity.

Acetylcholinesterase activity measurement: PC12 cells were detached from the substrate by trypsin treatment and washed twice with PBS. Cells were resuspended in 0.1M Na-phosphate buffer (pH 8.0) containing 1% Triton X-100 and sonicated for 20 seconds. For enzyme activity measurement, 5 μl cell homogenate was mixed with 190 μl of a 10 mM dithiobisnitrobenzoic acid solution (DTNB, Sigma) and 5 μl were transferred into a 96-well plate. After addition of 5 μl acetylthiocholine iodide (final concentration 0.5 M, Sigma) the change of absorbance at 412 nm was followed for 10 minutes.

Immunohistochemistry of AD slices: Slices of patients diagnosed with Alzheimer's disease and patients of the same age diagnosed negative for Alzheimer's disease were provided by the University Hospital Freiburg and were in obtained in accordance with institutional ethical guidelines. Paraffin embedded samples were stained according to the Bielschowsky's silver staining. Slices were deparaffinized and incubated in 10% silver nitrate solution for 15 minutes. After washing, samples were incubated for 30 minutes at 30° C. in an ammonium silver solution, treated with a developing solution followed by one minute incubation in 1% ammonia hydroxide to stop the silver reaction. After washing, slices were imaged immediately with a Zeiss Observer A1 (ZEISS AG, Germany) and with the AFM as described above.

Example 4 a) Inhibition of the Formation of Glial Scars

Glial scars are formed in vitro in a model system using meningeal fibroblasts and cortical astrocytes in the presence of TGF-beta. When these cells were plated on a surface with a nanoroughness of 32 nm Eq, they did not organize into glial scars (see also FIG. 1).

Figure 8:
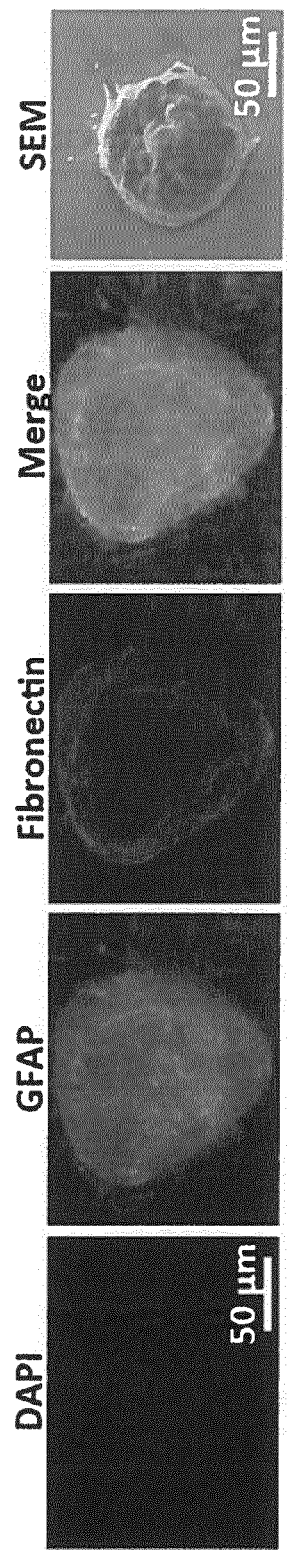
FIG. 8 shows glial scar formation in vitro using meningeal fibroblasts+cortical astrocytes+TFG-beta-1 (see Example 4 and also FIG. 1).

For the formation of glial scars in vitro, two primary cell types (meningeal fibroblasts and cortical astrocytes freshly isolated from rats) were seeded together in a cell culture dish on opposite sides of the dish. Once the cells grew together, TGF-β was added to the culture, and scar tissue formed within 24 hours. Afterwards these were stained with DAPI (visualizing the cell nucleus) and antibodies against GFAP (visualizing the astrocytes) and fibronectin (visualizing the fibroblasts). The SEM (scanning electron microscopy) shows the complete scar tissue for a better understanding of its morphology (FIG. 8).

b) Dissolution of Glial Scars

Pre-formed glial scars were then taken and placed on the 32 rq nanorough surface. After 24 hours, a dissociation was observed (see FIGS. 9 and 2).

Figure 9:
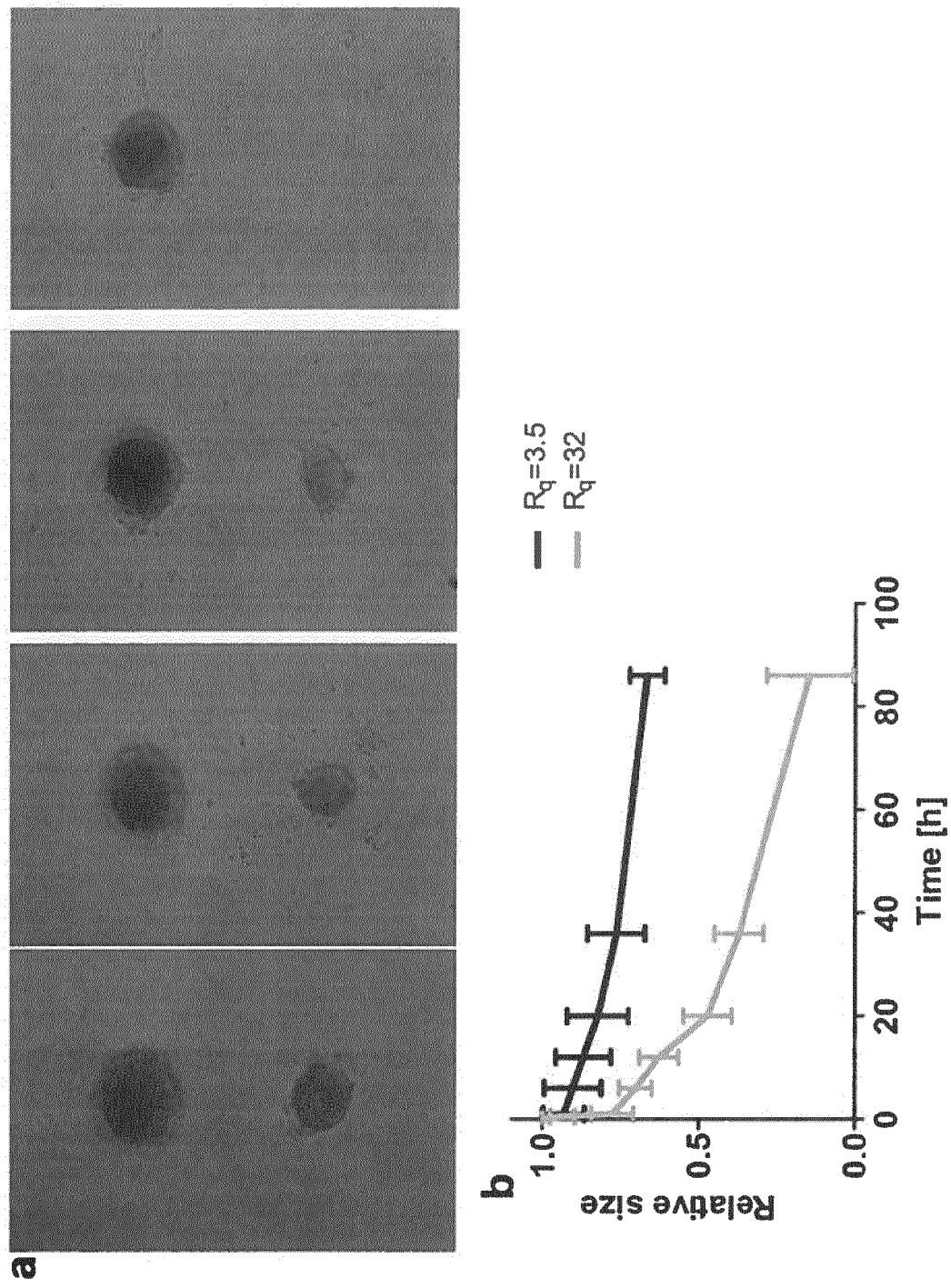
FIG. 9 shows glial scar dissociation upon replacing of existing scar clumps onto Rq=32 nm surfaces. (A) Optical micrographs, (B) Change in sphere size as a function of time (see also FIG. 2).

For the upper part of FIG. 9, cells, glial scars were generated as described above (on glass; Rq of glass=3.5 nm) and transferred onto another glass substrate, and observed over time. The lower scar tissue was also generated as described above, and transferred onto a surface with a nanoroughness of 32 nm. It can be seen that the size of the scar tissue decreases when it was transferred onto 32 nm substrates. After ~80 hours incubation, most of the scar tissues are 'dissolved', and it seems that cells are actively growing out of the scar tissue. This observation is quantified in the graph below (FIG. 9) indicating that scar tissue that was re-seeded onto glass also very slightly reduced in size. However, scar tissue re-seeded onto Rq=32 nm dissolved in the majority of cases.

Both these findings are significant with respect coatings for neural implants and treatment of spinal injuries as they show that stochastic nanoroughness in a certain regime can both mitigate formation of glial scar, but also absolve the formed glial scar.

Example 5

Figure 10:
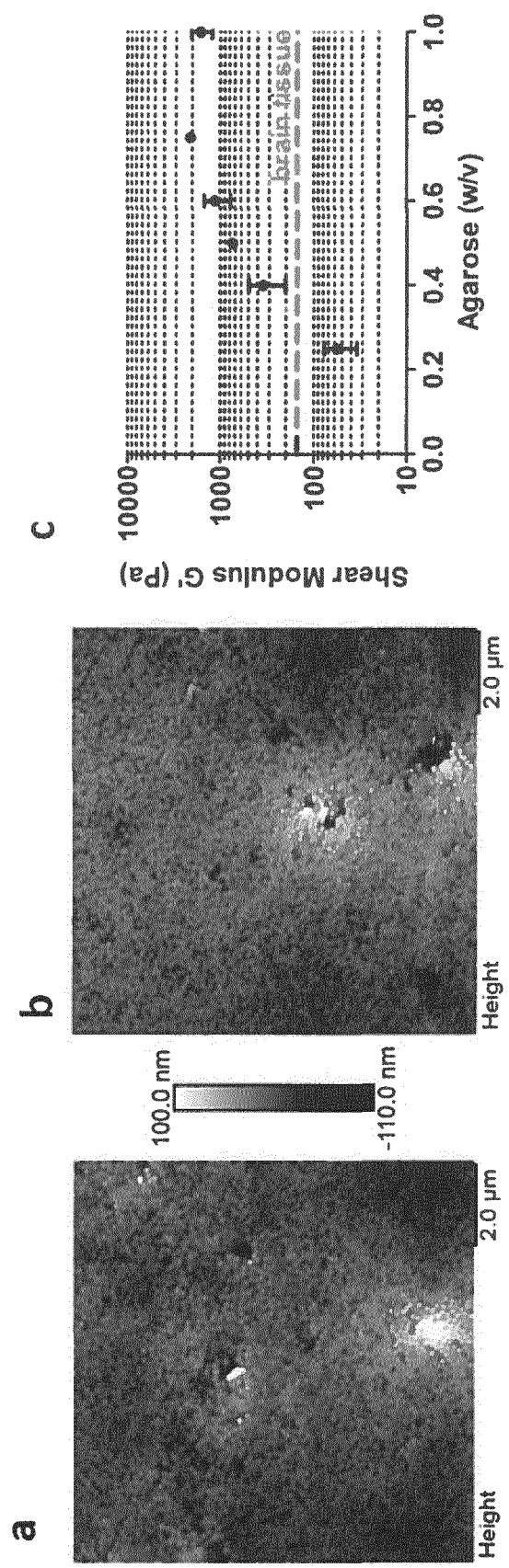
FIG. 10 shows AFM of dip-coated electrodes with an Rq of 32 nm before (left) and after (right) "implantation" into agarose gels for 4 weeks, and rheology of different agarose gels.
Figure 11:
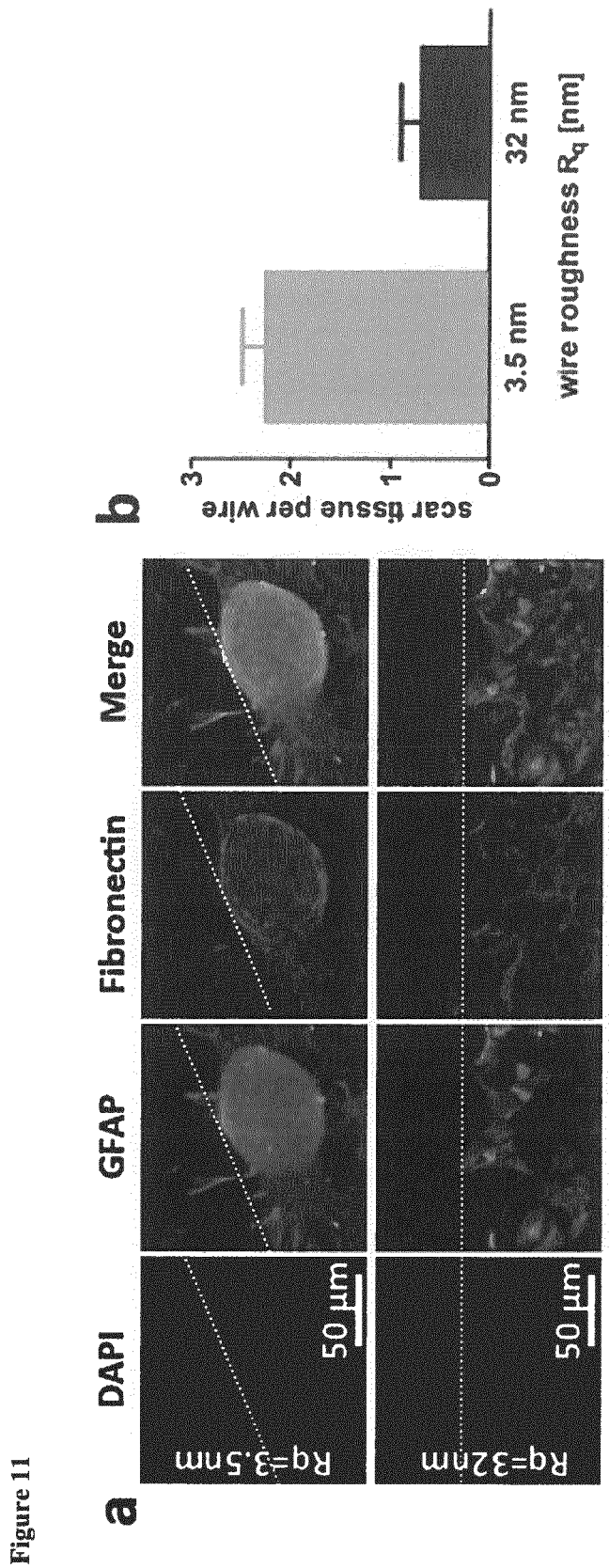
FIG. 11 shows glial scar formation on non-coated (top) vs. coated (bottom) polymer wires (A), and quantification of scar built-up (B) (see also FIG. 2).
Figure 12:
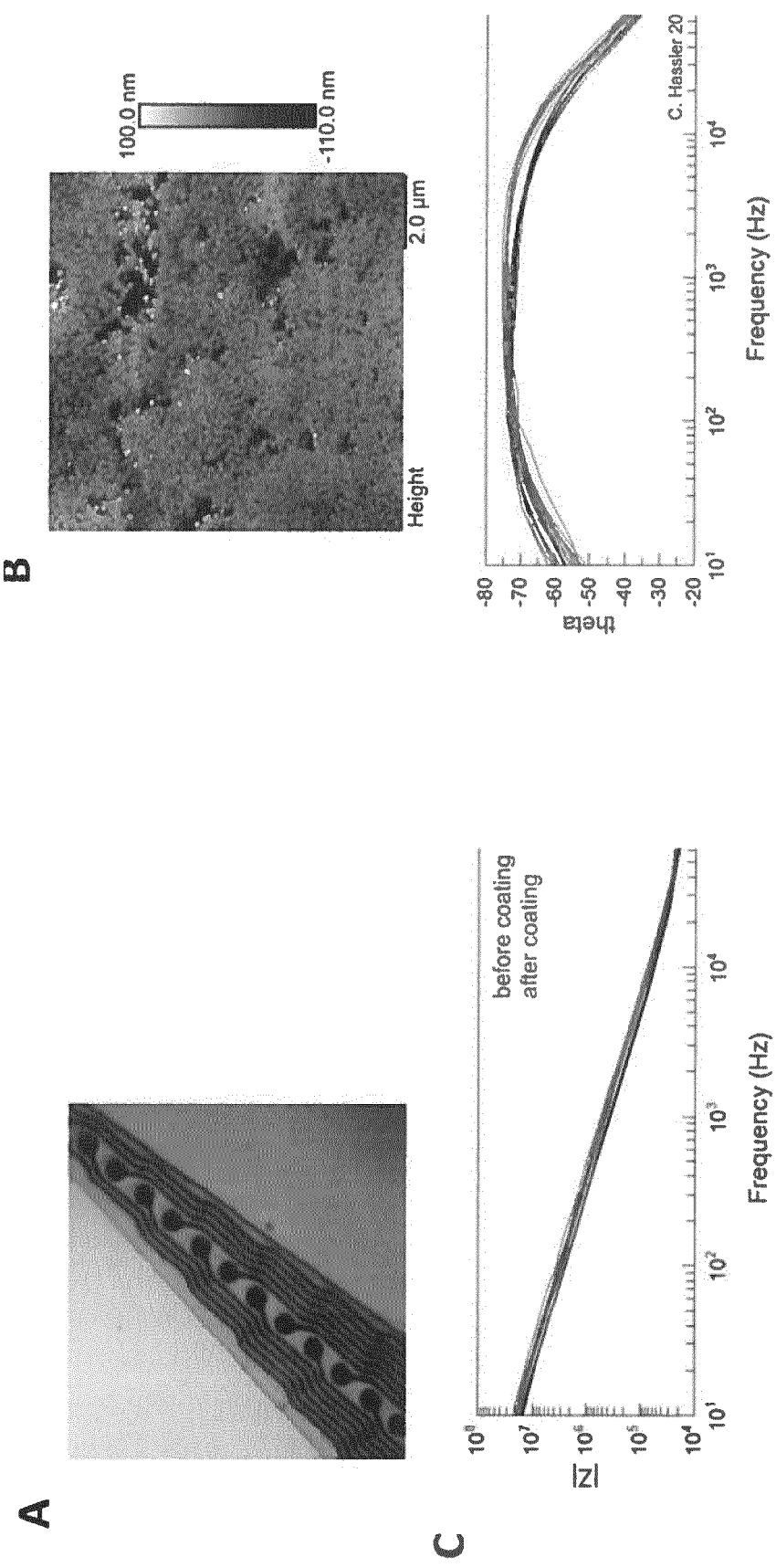
FIG. 12 shows an optical micrograph of 15-pol electrode (A), AFM of 15-pol electrode dip-coated with silica nanoparticles to create a surface roughness of Rq=32 nm (B), and impedance measurements before (C), and after nanoparticle coating (D).

Coating of Electrodes and Wires for Implantation (See FIGS. 10 to 12)

Electrodes (15-pol microelectrodes) were dip-coated with SNPs thus creating an electrode surface roughness of 32 nm. This was confirmed with AFM (a). These electrodes were then 'implanted' into agarose gels for 4 weeks. These agarose gels had the same shear modulus as normal brain tissue has (c). In order to verify the coating integrity of the electrodes AFM was performed again (b). This experiment should show that coating microelectrodes with SNPs can persist implantation into brain (as is the supposed usage) while keeping the coating intact (FIG. 10).

FIG. 12 shows (A) a picture of the 15-pol microelectrode as mentioned above. (B) SNP coating of the electrode and AFM scanning micrograph of the same as described above. (C) Impedance of the electrodes before (black graphs) and after (red graphs) coating with SNPs. (D) Theta-measurement of the electrodes before (black graphs) and after (red graphs) coating with SNPs. The graphs show that coating the electrodes with SNPs does not alter the impedance or the theta of the electrodes, thus not changing their behaviour regarding the intended use as brain stimulators.

As shown in FIG. 11, (a) glial scars were created as described above. A polymer wire was introduced into the cell culture dish (the white dotted line represents the position of the polymer wire before removing it for better visualization of the cells). This wire was either coated with SNPs (thus having a surface roughness of Rq=32 nm) or not coated. Over a variety of experiments, significantly more scar tissue was formed on non-coated polymer wires compared to coated polymer wires with a surface roughness of 32 nm (b).

Example 6

U-87 Spheroid Matrigel Invasion Assay

Figure 5:
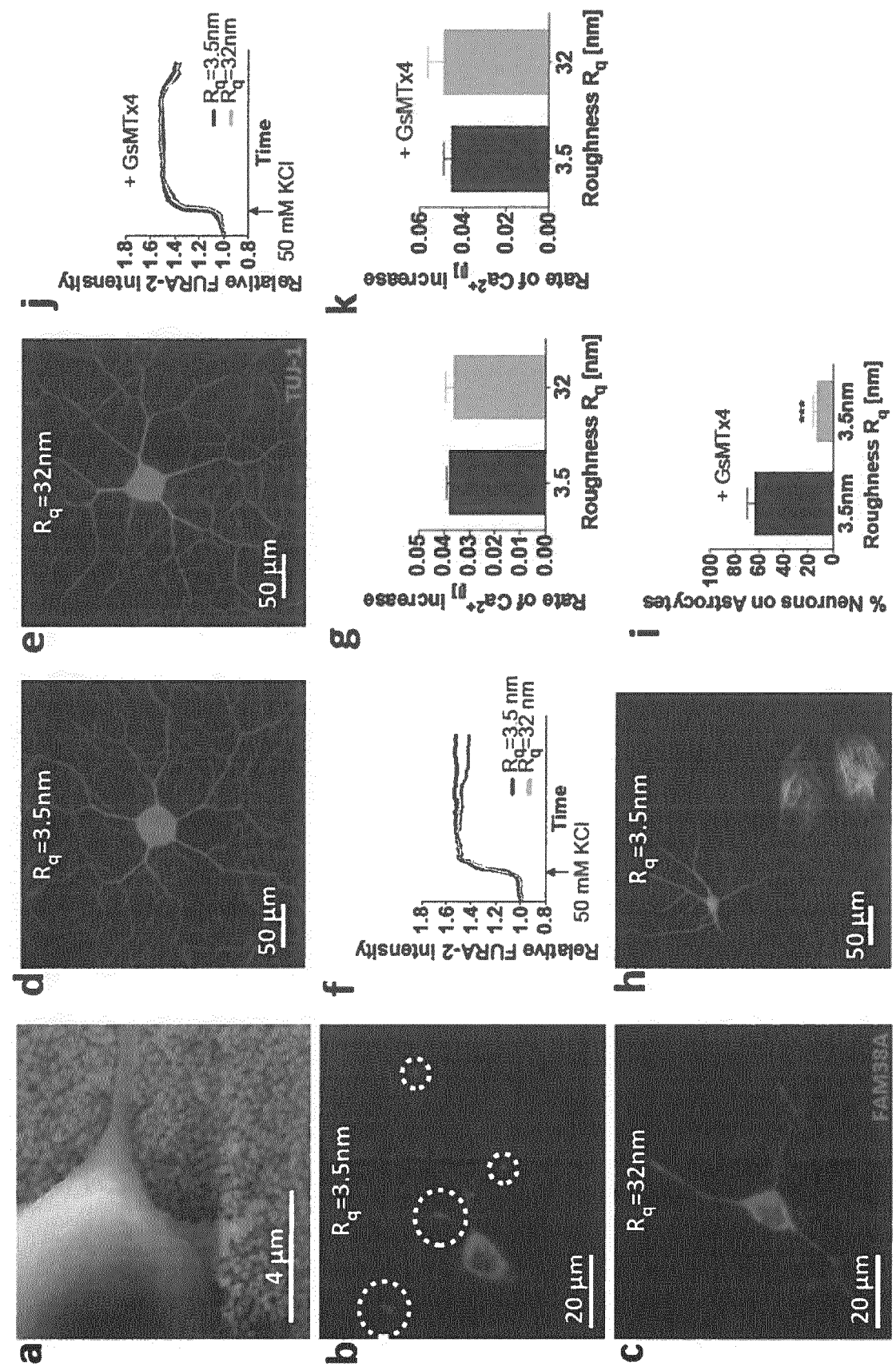
Figure 13:
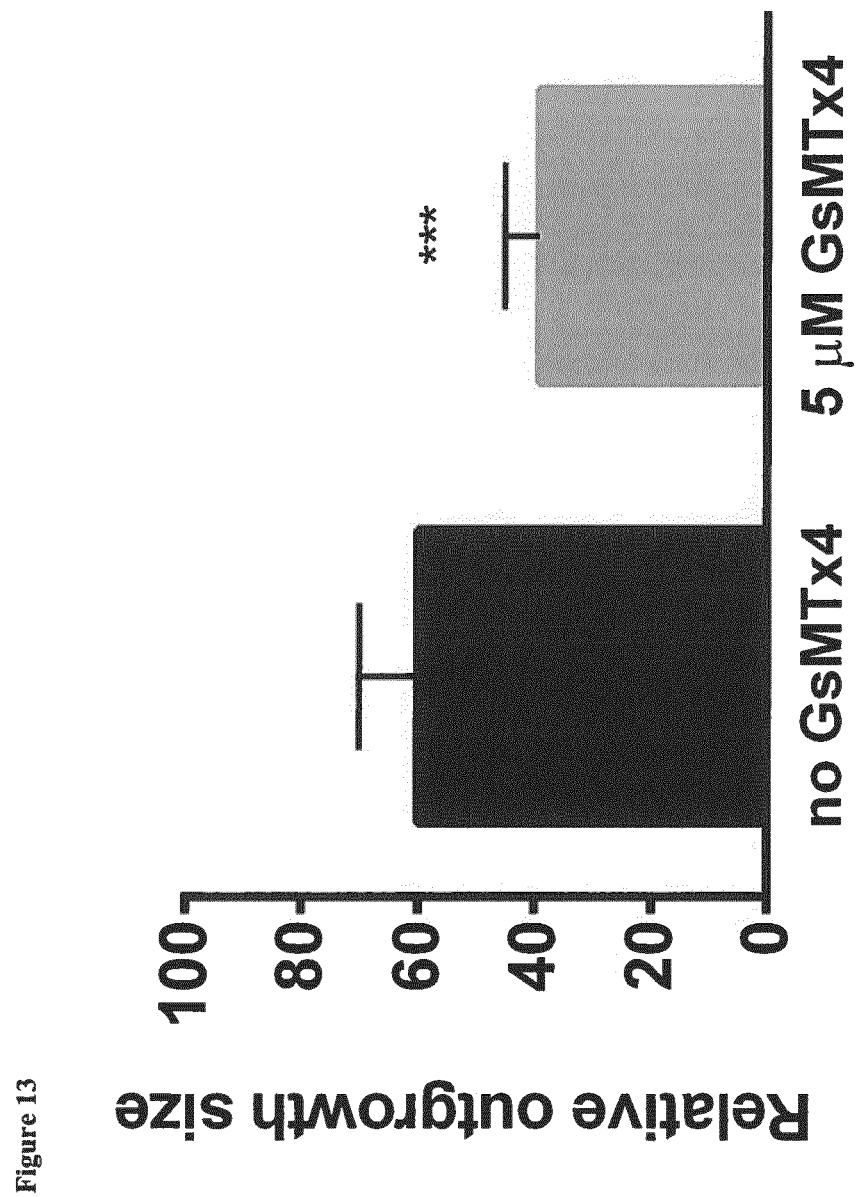
FIG. 13 shows the formation of sprouts from GMB tumor spheroids, which is an indication of invasiveness migration in the presence or absence of the spider venom toxin GsMTx4 which inhibits Piezo-1.

The formation of sprouts from GMB tumor spheroids which is an indication of invasiveness (Invasion assay) was significantly reduced in presence of the spider venom toxin GsMTx4 which inhibits many cation channels, including Piezo-1 (FIGS. 13, and 5).

Spheroids (which resemble a GBM tumor in vitro) are formed via the hanging drop procedure. For this, cells were seeded into a carboxymethylcellulose solution (with very high viscosity) and pipetted on the inner side of the lid of a cell culture plate. After reversing the lid and putting it back onto the cell culture plate, the cells are hanging in a drop of carboxymethylcellulose. Because of the high viscosity of the media and no possibility to attach, the cells form spheroids. These spheroids were washed and re-seeded into a 3D matrix of collagen I and carboxymethylcellulose. During incubation cells start migrating out of the spheroid and invading the 3D matrix. The higher the invasive potential of the cells, the more they will invade the 3D matrix. It is obvious that cell have less invasive potential when GsMTx4 (a spider venom that blocks mechanosensitive channels) is added to the culture media.

Example 7

Knock-Down of Piezo-1

Figure 7:
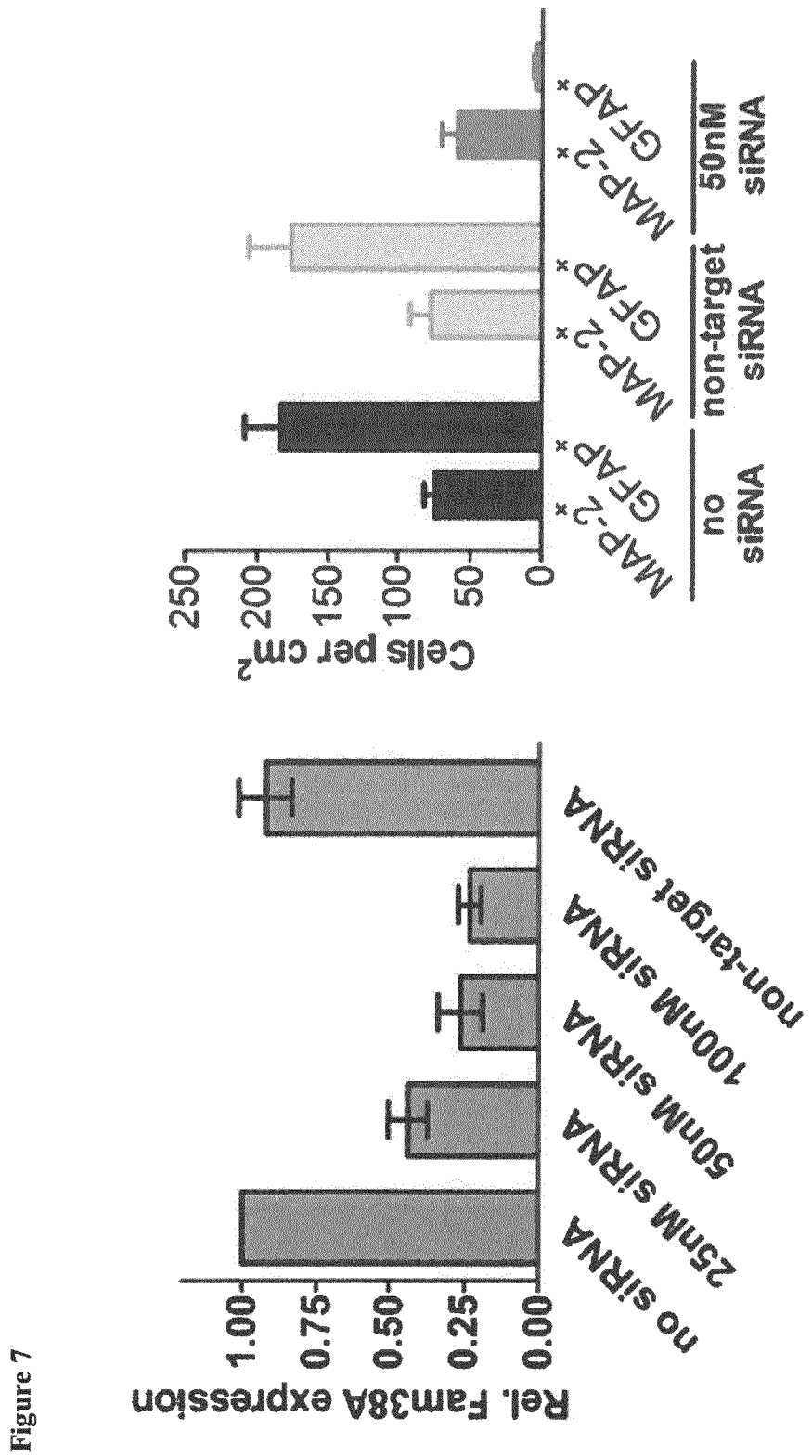
FIG. 7 shows the results of the siRNA knockdown of FAM38 in Astrocyte/Hippocampal neuron co-cultures (see Example 3).

In a second assay, regarding Piezo-1, using glioblastoma multiforme (GBM) cell lines and primary GBM cells (KF) from human tumor explants of various aggressiveness, it was shown that their migration (through matrigel/collagen in a trans well migration assay) can be completely stopped by knocking down (silencing) piezo-1 (see FIGS. 7, and 14).

The experimental set-up was a classical transwell migration assay. A 24-well plate insert with a membrane (8 um pore size) was coated with Matrigel, forming a 3D matrix. After Matrigel was jellified, cells (U-87, GBM (GBM-1), KF (GBM-2)) were seeded in the top of the Matrigel (the media in which the cells are seeded was either supplemented with siRNA against FAM38A or without any additional agent). Below the membrane was medium, either supplemented with an attractant (in this case the chemoattractant was FBS) or no attractant. Over a time of 24 hours, the cells were incubated and the ones that migrated through the Matrigel and attached to the membrane were stained with DAPI and quantified. The bigger the amount of migrated cells, the bigger their migratory potential). The graph shows that with chemoattractant and without siRNA the cells strongly migrate through the Matrigel. Without chemoattractant, less cells migrate through, and this movement was only due to random motion of the cells. The use of FAM38A-siRNA clearly reduced the migratory potential of all three cells lines used. Since the extraordinary high capacity of glioblastoma cells to migrate and invade surrounding tissue is the hallmark of GBM, reducing this capacity indicate an interesting pharmaceutic target, i.e. provides evidence for a use of Piezo-1 as a target for treating brain tumors and especially GBM.

What is claimed is:

1. A neural implant comprising a biomaterial selected from the group consisting of platinum, gold, and a synthetic polymer,
wherein said biomaterial has an outer surface with a stochastic nanoroughness (Rq) of 32 nm.

2. The neural implant according to claim 1, wherein said biomaterial is the synthetic polymer that comprises an active substance that is part of the biomaterial, wherein said active substance is an antimicrobial agent, and wherein said biomaterial retains the outer surface having the stochastic nanoroughness (Rq) of 32 nm.

3. The neural implant according to claim 1, wherein said synthetic polymer is selected from the group consisting of a polymer wire, a nanotube, an array of micro-sized posts or pillars, carbon fibers, and composite carbon nanofibers.

4. The neural implant according to claim 1,
wherein said neural implant is selected from the group consisting of an electrode, a pacemaker, and a drug delivery device, and
wherein said biomaterial is applied to the surface of said neural implant as a coating that retains the stochastic nanoroughness (Rq) of 32 nm.

5. The neural implant according to claim 4, wherein said electrode is selected from the group consisting of a measuring electrode and a stimulating electrode.

6. The neural implant according to claim 5, wherein said electrode is a flexible nanoelectrode.

7. The neural implant according to claim 1, wherein said neural implant consists essentially of said biomaterial.

8. The neural implant according to claim 1, wherein said stochastic nanoroughness (Rq) is applied to said biomaterial using a method selected from the group consisting of polishing, machining, surface treatment, coating, cathodic polarization, acid etching, rolling, atmospheric plasma, laser treatment, and casting.

9. A method for the diagnosis or treatment of a neurological disorder, said method comprising positioning a neural implant of claim 1 at a treatment location and obtaining, acquiring, and/or delivering signals to arrive at a diagnosis and/or treatment of said neurological disorder,
wherein said neurological disorder is selected from the group consisting of Parkinson's disease, Alzheimer's disease, glioblastoma, and glial scars.

10. The neural implant of claim 1, wherein said synthetic polymer is selected from the group consisting of a poly(organo)siloxane, an antimicrobial polymer, poly(3,4-ethylene dioxythiophene) (PEDOT), polyterthiophene (PTTh), polypyrrole (PPy), and a PPy derivative.

11. The neural implant according to claim 10,
wherein said PPy derivative is selected from the group consisting of cyclotene and parylene C.

12. The neural implant according to claim 1, wherein said biomaterial is applied as a coating to the surface of said neural implant.

13. The neural implant according to claim 1,
wherein said neural implant is selected from the group consisting of an electrode, a pacemaker, and a drug delivery device that is formed from said biomaterial and
wherein said electrode, pacemaker, or drug delivery device retains the outer surface with the stochastic nanoroughness (Rq) of 32 nm.

14. The neural implant according to claim 13, wherein said electrode is selected from the group consisting of a measuring electrode and a stimulating electrode.

* * * * *